(12) United States Patent
Whelton

(10) Patent No.: US 10,932,985 B1
(45) Date of Patent: Mar. 2, 2021

(54) SYSTEMS AND METHODS OF POSITIONING A BODY OF A USER DURING STIMULATION FOR THERAPEUTIC EFFECTS

(71) Applicant: Ryan Whelton, Land O Lakes, FL (US)

(72) Inventor: Ryan Whelton, Land O Lakes, FL (US)

(*) Notice: Subject to any disclaimer, the term of this patent is extended or adjusted under 35 U.S.C. 154(b) by 0 days.

(21) Appl. No.: 16/819,063

(22) Filed: Mar. 14, 2020

(51) Int. Cl.
*A61N 1/36* (2006.01)
*A61H 9/00* (2006.01)

(52) U.S. Cl.
CPC ....... *A61H 9/0078* (2013.01); *A61N 1/36021* (2013.01); *A61H 2201/10* (2013.01); *A61H 2201/1261* (2013.01); *A61H 2201/165* (2013.01); *A61H 2205/02* (2013.01); *A61H 2205/04* (2013.01); *A61H 2205/06* (2013.01); *A61H 2205/062* (2013.01); *A61H 2205/065* (2013.01); *A61H 2205/067* (2013.01); *A61H 2205/081* (2013.01); *A61H 2205/083* (2013.01); *A61H 2205/086* (2013.01); *A61H 2205/088* (2013.01); *A61H 2205/10* (2013.01); *A61H 2205/12* (2013.01)

(58) Field of Classification Search
CPC .............. A61H 9/0078; A61H 2201/10; A61H 2201/1261; A61H 2201/165; A61H 2205/02; A61H 2205/04; A61H 2205/06; A61H 2205/062; A61H 2205/065; A61H 2205/067; A61H 2205/081; A61H 2205/083; A61H 2205/086; A61H 2205/088; A61H 2205/10; A61H 2205/12; A61N 1/36021
See application file for complete search history.

(56) References Cited

U.S. PATENT DOCUMENTS

| | | | | |
|---|---|---|---|---|
| 9,345,872 | B2* | 5/2016 | Groteke | A61N 1/0476 |
| 9,675,802 | B2* | 6/2017 | Crowe | A61N 1/321 |
| 2002/0077688 | A1* | 6/2002 | Kirkland | A61N 1/0456 607/142 |
| 2005/0187071 | A1* | 8/2005 | Yamashita | D04B 1/102 482/1 |
| 2007/0287900 | A1* | 12/2007 | Breen | A61B 5/4528 600/407 |
| 2013/0204169 | A1* | 8/2013 | Poepperling | A61H 23/02 601/46 |
| 2015/0366504 | A1* | 12/2015 | Connor | A61B 5/0492 600/301 |
| 2017/0312161 | A1* | 11/2017 | Johnson | A61H 7/001 |
| 2018/0153445 | A1* | 6/2018 | Noda | A61B 5/1124 |

* cited by examiner

*Primary Examiner* — Ankit D Tejani
*Assistant Examiner* — Joshua Brendon Solomon
(74) *Attorney, Agent, or Firm* — Tiffany C. Miller; Inventions International Inc.

(57) ABSTRACT

A method of stimulation of a body of a user for therapeutic effects having the steps of providing a stimulator connected to a garment. The garment is connected to a first predetermined location on a user's body. Positioning a user's body at a predetermined orientation. The next step includes applying stimulation from the stimulator to the first predetermined location on the user's body so that therapeutic effects are experienced at both the first predetermined location and at a second predetermined location of a user's body.

24 Claims, 23 Drawing Sheets

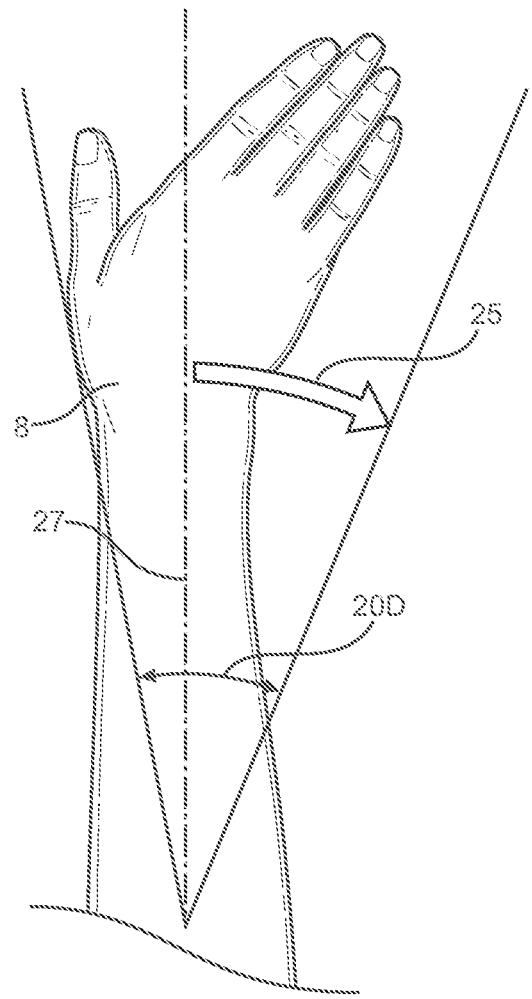
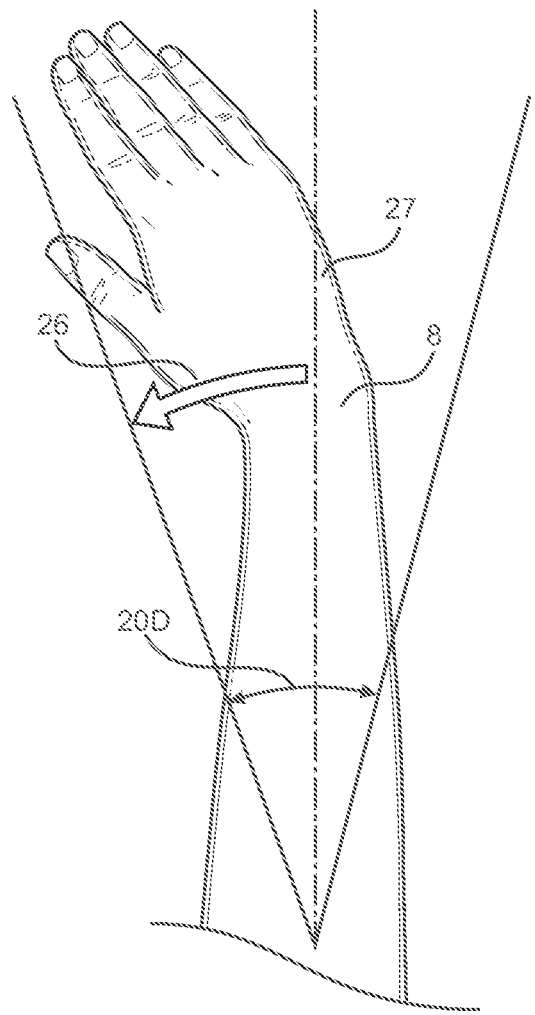
FIG. 5A
FIG. 5B

US 10,932,985 B1

SYSTEMS AND METHODS OF POSITIONING A BODY OF A USER DURING STIMULATION FOR THERAPEUTIC EFFECTS

BACKGROUND OF THE INVENTION

1. Field of the Invention

This invention relates, generally, to positioning of a user's body during stimulation for therapeutic effects. More particularly, it relates to an electrical stimulation device connected to a garment having an electrode which emits electrical current to a first portion of the body to provide relief of pain to the first portion and a second portion of the body when the user's body is oriented in a predetermined position.

2. Background Art

Electrical stimulators are used as an electrotherapy treatment method for pain. Frequency refers to the pulses produced per second during stimulation and is stated in units of Hertz (Hz). Electrical stimulators in today's market include electrode pads which may be adhered to a user's body and emit electrical current to a site of pain of a user's body. It is also known for electrodes of an electrical stimulator to be incorporated into a glove to be received by a user's hand during treatment. However, current methods of electrotherapy include the electrodes of an electrical stimulator to be applied directly to individual areas of pain on a user's body while the user is laying down or oriented in a seated position during electrotherapy treatment sessions. It would be more desirable to facilitate the optimal stimulation of a desired body part for the most effective pain relief of a plurality of areas. Thus, there is a need for an improved electrotherapy treatment method for pain relief of a user requiring the user's body to be oriented in a predetermined position during electrical stimulation or any other type of stimulation having a therapeutic effect on a user's body.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for a method of stimulation of a body of a user for therapeutic effects having the steps of providing any stimulator such as an electrical stimulator. It is within the scope of this invention for this method of stimulation to provide therapeutic effects including, but not limited to, pain relief, increased healing rate, wound healing, increased range of motion function, or decreased inflammation. The electrical stimulator is electrically connected to electrodes. Providing a garment. The garment is connected to the electrodes of the electrical stimulator. The garment is connected to a first predetermined location on a user's body. Positioning a user's body at a predetermined orientation. The predetermined orientation includes the steps of positioning at least one finger of the user between 0-120 degrees of flexion or between 0-35 degrees of extension, positioning at least one wrist of the user between 0-50 degrees of extension or 0-85 degrees of flexion, positioning at least one wrist of the user between 0-88 degrees of pronation or between 0-88 degrees of supination, positioning at least one wrist of the user between 0-28 degrees of ulnar deviation or between 0-18 degrees of radial deviation, positioning at least one elbow of the user between 0--3 degrees of hyperextension or between 0-130 degrees of flexion, positioning at least one shoulder of the user between 0-145 degrees of shoulder abduction or between 0-45 degrees of shoulder adduction, positioning at least one shoulder of the user between 0-145 degrees of shoulder flexion or between 0-58 degrees of extension, and positioning at least one shoulder of the user between 0-85 degrees shoulder of external rotation or between 0-50 degrees of internal rotation. The next step includes applying electrical current from the electrical stimulator to the first predetermined location on the user's body so that pain relief is experienced at both the first predetermined location and at a second predetermined location of a user's body, and which also includes improvements that overcome the limitations of prior art systems and methods of electrical stimulation for pain relief is now met by a new, useful, and non-obvious invention.

The method of electrical stimulation of a body of a user for pain relief includes the garment including, but not being limited to, a sleeve, a sock, a cap, a hat, a glove, or a pad. It is within the scope of this invention for the garment to be electrically conductive. It is within the scope of this invention for the garment to be capable of emitting any form of stimulation to a user's body resulting in a therapeutic effect.

The method of electrical stimulation of a body of a user for pain relief includes the first predetermined location on the user's body is at least a portion of an arm. The sleeve receives at least a portion of the arm of the user. The predetermined location on the user's body can be at least a portion of a finger. The sleeve receives at least a portion of the finger of the user. The first predetermined location on the user's body can also be a hand. The glove receives at least one hand of the user. The first predetermined location on the user's body can also be at least a portion of a shoulder of a user.

In an alternate embodiment, the garment is connected to a simulator emitting any stimulation including, but not limited to, a light, an electrical current, a laser, or a vibration to the first predetermined location on the user's body.

In another embodiment, the garment is pneumatically actuated to constrict, including, but not limited to, intermittent or constant, at a first predetermined location on the user's body. It is within the scope of this invention for the garment to be configured to constrict at least a portion of a user's body by any means including, but not limited to pneumatically.

BRIEF DESCRIPTION OF THE DRAWINGS

For a fuller understanding of the nature and objects of the invention, reference should be made to the following detailed description, taken in connection with the accompanying drawings, in which:

FIG. 5A is a range of motion diagram of the predetermined orientation 20D of a user's body during positioning of a wrist of a user between 0-28 degrees of ulnar deviation;

FIG. 5B is a range of motion diagram of the predetermined orientation 20D of a user's body during positioning of a wrist of a user between 0-18 degrees of radial deviation;

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Figure 1:
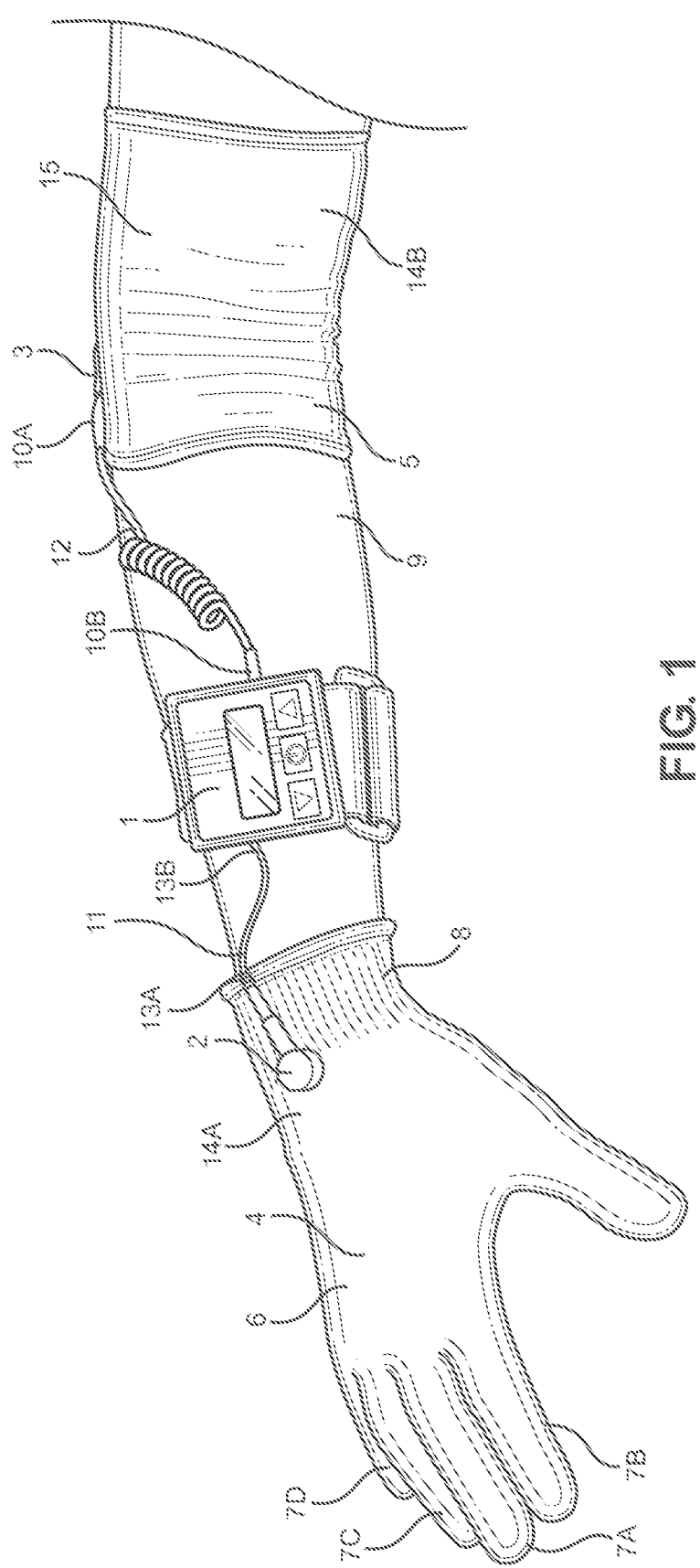
FIG. 1 is a perspective view of a user wearing an electrically conductive garment being a glove and a sleeve, an electrical stimulator has an electrode connected to a glove and another electrode is connected to a sleeve.

In a general embodiment, the novel method of electrical stimulation of a body of a user for pain relief has the steps of providing an electrical stimulator 1. As best shown in FIG. 1, electrical stimulator 1 is electrically connected to a garment. Electrical stimulator 1 may be any type of electrotherapy unit capable of emitting electrical impulses at any waveform, any frequency, any pulse amplitude, or any pulse width. Electrical stimulator 1 is electrically connected to at least one electrode with an electrical cord. It is within the scope of this current invention for the electrode to include, but not be limited to, sponge electrodes. In an example, sponge electrodes are configured for the transfer of direct electrical current from the stimulator to a user. It is within the scope of this invention for an electrode to include, but not be limited to, a probe, a sponge, or a pin electrode connector on an adhesive pad. First electrical cord 11 has first end 13A located opposite second end 13B. First electrical cord 11 has first end 13A connected to first electrode 2. First electrode 2 is connected to glove 4. First electrical cord 11 has second end 13B connected to electrical stimulator 1. Second electrical cord 12 has first end 10A located opposite second end 10B. Second electrical cord 12 has first end 10A connected to second electrode 3. Second electrode 3 is connected to sleeve 5. Second electrical cord 12 has second end 10B connected to electrical stimulator 1. It is within the scope of this current invention for a garment to be connected to electrodes 2 and 3 of electrical stimulator 1. A garment includes, but is not limited to, a band, a pad, a sleeve, a wrap, a glove, a sock, a boot, a cap, or a hat. The garment is connected to a first predetermined location on a user's body. It is within the scope of this invention for this novel method to provide a stimulator capable of stimulation including, but not limited to, electrical, light, vibration, or laser. It is within the scope of this invention for this method of stimulation to provide therapeutic effects including, but not limited to, pain relief, increased healing rate, wound healing, increased range of motion function, or decreased inflammation. It is within the scope of this current invention for the garment to be configured to wirelessly communicate with the stimulator using including, but not limited to, Bluetooth, electromagnetic frequencies, or radio waves.

FIG. 1 illustrates user's hand 6 and user's fingers 7A-7D are received by garment being glove 4. At least a portion of user's wrist 8 is received by glove 4. Electrical stimulator 1 may be worn by a user or it maybe located at a remote site that is not located on a user. It is required that at least one electrode of electrical stimulator 1 is in electrical communication such as, wired with an electrical cord or wireless with a user's body when a user's body is positioned at a predetermined orientation. In a preferred embodiment, novel acupuncture points are electrically stimulated by the electrodes of electrical stimulator 1. These novel acupuncture points may be accessed by the electrical stimulator 1 when the user's body is specifically positioned within a range of motion. When a user's body is positioned to a predetermined orientation corresponding to novel acupuncture points or other points including, but not limited to, trigger points or myofascial points, the electrical stimulation is applied to predetermined locations of a user's body to relieve pain at both the predetermined location and at other associated sites of a user's body as described as this description proceeds.

FIG. 1 illustrates user's arm 9 receives garment being sleeve 5. It is within the scope of this current invention for user 47 (FIG. 8) to include any person or patient receiving stimulation at novel body positioning predetermined orientations. This method includes therapeutic effects at a specific area by using for example, an electromagnetic field at a remote site at another specific area. Connections in the human nervous system are utilized to treat pain at one location of the body by applying electromagnetic fields to a different part of the human body. Further, application of the electromagnetic field to a plurality of adjacent areas of the body is sufficient to provide therapeutic effects throughout the body. In an example, certain locations on the human foot are linked to a number of other locations. By applying electromagnetic fields to the predetermined location of the foot, pain at the predetermined location and pain at a plurality of different locations will be relieved. If sufficient area of the foot is treated with the electromagnetic field, such with an electrically conductive sock in communication with an electrical stimulator, then the pain may be relieved throughout the entire body.

In a first embodiment, FIG. 1 shows electrically conductive glove 4 may be the garment to be worn by a user's hand to electrically stimulate first predetermined location 14A or 14B including, but not limited to, the medial and lateral aspect of the fingers and hand, the anterior and posterior aspect of the fingers and hand, the medial and lateral aspect of the wrist, the anterior and posterior aspect of the forearm, the anterior and posterior aspect of the wrist, the medial and lateral aspect of the forearm, the medial and lateral aspect of the elbow, and/or the anterior and posterior aspect of the elbow. Other first predetermined locations 14 within the scope of this first embodiment of the novel method include, but are not limited to, the medial and lateral bicep and tricep, the anterior and posterior bicep and tricep, the medial and lateral shoulder, and/or the anterior and posterior shoulder. Electrically conductive glove 4 is in electrical communication with electrical stimulator 1. The connection between the garment and the stimulator may be wired using an electrical cord or wireless. In other words, electrical stimulation may be applied to many acupuncture points in the hand, fingers, and wrist when electrically conductive glove 4 is worn on first predetermined location 14A or 14B on a user's body. In this example, FIG. 1 illustrates electrically conductive glove 4 having first predetermined location 14A being a user's hand, fingers, and wrist or first predetermined location 14B may be user's elbow 15. The first predetermined location 14 of a user's body is in contact with the electrically conductive garment and is electrically stimulated by electrical stimulator 1.

In this first embodiment, when first predetermined location 14 of a user's body is electrically stimulated by electrical stimulator 1 in electrical communication with garment being glove 4, therapeutic effects are experienced at both the first predetermined location 14 and at second predetermined location 42. It is within the scope of this invention for all embodiments to include therapeutic effects experienced at a plurality of predetermined locations. It is within the scope of this first embodiment of the current invention for the second predetermined location 42 to include, but not be limited to at least one of, the bilateral medial and lateral aspect of the fingers, toes, feet, calves, shins, knees, thighs, hands, neck, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral aspect of the fingers and/or hand.

In this first embodiment, when first predetermined location 14 of a user's body is electrically stimulated by electrical stimulator 1 in electrical communication with garment being glove 4, therapeutic effects are experienced at both the first predetermined location 14 and at second predetermined location 42. It is within the scope of this first embodiment of the current invention for the second predetermined location 42 to include, but not be limited to, the bilateral anterior and posterior and aspect of the fingers, toes, feet, thighs, hands, neck, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior aspect of the fingers and/or hand.

In this first embodiment, when first predetermined location 14 of a user's body is for example, electrically stimulated by electrical stimulator 1 in electrical communication with a garment, therapeutic effects are experienced at both the first predetermined location 14 and at second predetermined location 42. It is within the scope of this first embodiment of the current invention for the second predetermined location 42 to include, but not be limited to, bilateral anterior and posterior aspect of fingers, toes, feet, calves, shins, thighs, hands, neck, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior aspect of the wrist.

In this first embodiment, when first predetermined location 14 of a user's body is for example, electrically stimulated by electrical stimulator 1 in electrical communication with a garment, therapeutic effects are experienced at both the first predetermined location 14 and at second predetermined location 42. It is within the scope of this first embodiment of the current invention for the second predetermined location 42 to include, but not be limited to, bilateral medial and lateral aspect of fingers, toes, feet, calves, shins, thighs, hands, neck, knees, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral aspect of the wrist.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral anterior and posterior aspect of fingers, toes, thighs, hands, neck, feet, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior aspect of the forearm.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral medial and lateral aspect of fingers, toes, feet, calves, thighs, hands, neck, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral aspect of the forearm.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral medial and lateral aspect of the fingers, toes, feet, calves, thighs, hands, neck, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral aspect of the elbow.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral anterior and posterior aspect of the fingers, toes, thighs, hands, neck, feet, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior aspect of the elbow.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral medial and lateral aspect of the fingers, toes, thighs, hands, neck, feet, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral bicep/tricep.

In this first embodiment, when first predetermined location 14 of a user's body is for example, electrically stimulated by electrical stimulator 1 in electrical communication with a garment is sleeve 5 or pad, therapeutic effects are experienced at both the first predetermined location 14 and at second predetermined location 42. It is within the scope of this first embodiment of the current invention for the second predetermined location 42 to include, but not be limited to, bilateral anterior and posterior aspect of the fingers, toes, feet, thighs, hands, neck, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior bicep/tricep.

In this first embodiment, when first predetermined location 14 of a user's body is for example, electrically stimulated by electrical stimulator 1 in electrical communication with a garment is a pad, therapeutic effects are experienced at both the first predetermined location 14 and at second predetermined location 42. It is within the scope of this first embodiment of the current invention for the second predetermined location 42 to include, but not be limited to, bilateral medial and lateral aspect of the fingers, toes, feet, thighs, hands, neck, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the medial and lateral shoulder.

In this first embodiment, when first predetermined location 14 of a user's body is for example, electrically stimulated by electrical stimulator 1 in electrical communication with a garment is a pad, therapeutic effects are experienced at both the first predetermined location 14 and at second predetermined location 42. It is within the scope of this first embodiment of the current invention for the second predetermined location 42 to include, but not be limited to, bilateral anterior and posterior aspect of the fingers, toes, feet, thighs, hands, neck, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior shoulder.

Figure 2:
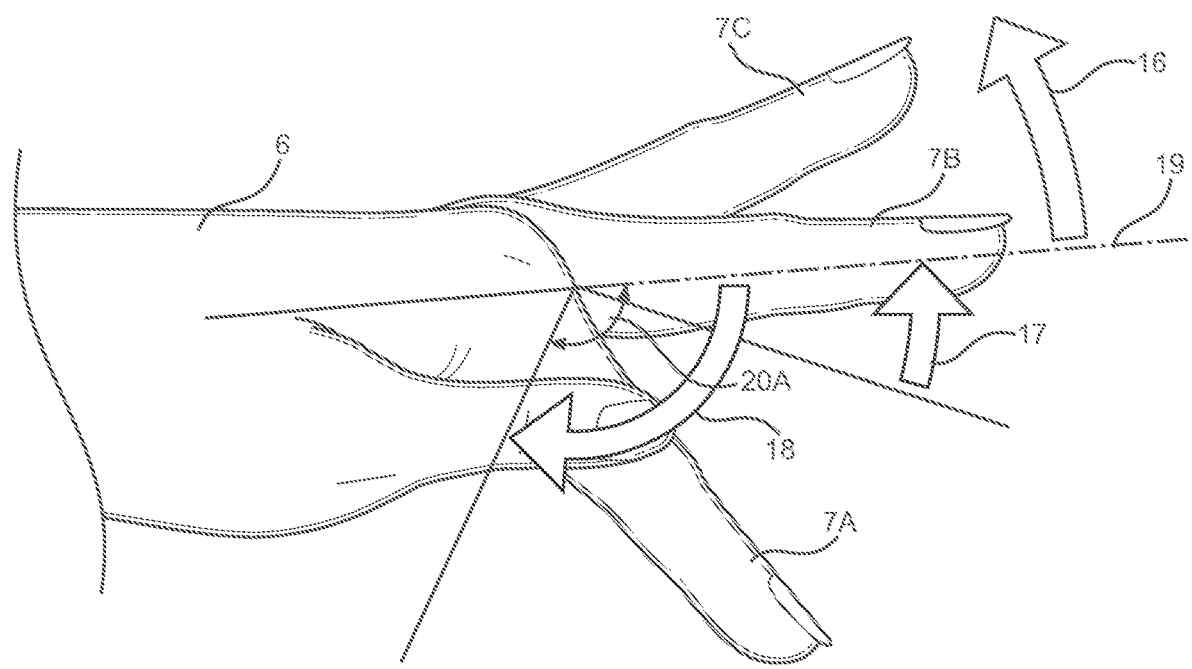
FIG. 2 is a range of motion diagram of the predetermined orientation 20A of a user's body positioning a finger of a user between 0-120 degrees of flexion or between 0-35 degrees of extension.

The next step in the first embodiment is to orient a user's body to a predetermined orientation 20A. FIG. 2 shows the predetermined orientation 20A of a user's body having positioning of at least one finger 7A of a user between 0-120 degrees of flexion 18 or between 0-35 degrees of extension 17. It is within the scope of this invention for predetermined orientation 20A of a user's body to include positioning of at least one finger 7A of a user between 120 degrees of flexion and 35 degrees of extension to include finger positioning between 0-90 degrees of flexion or finger positioning between 0-30 degrees of extension. FIG. 2 illustrates the definition of angles of a user's finger 7 positioning at hyperextension 16 and at 0 degrees 19 in which the user's finger positioning is straight or in a locked orientation. It is within the scope of this invention for the at least one finger to include, but not be limited to, at least one of the distal phalanx, the middle phalanx, or the proximal phalanx.

Figure 3A:
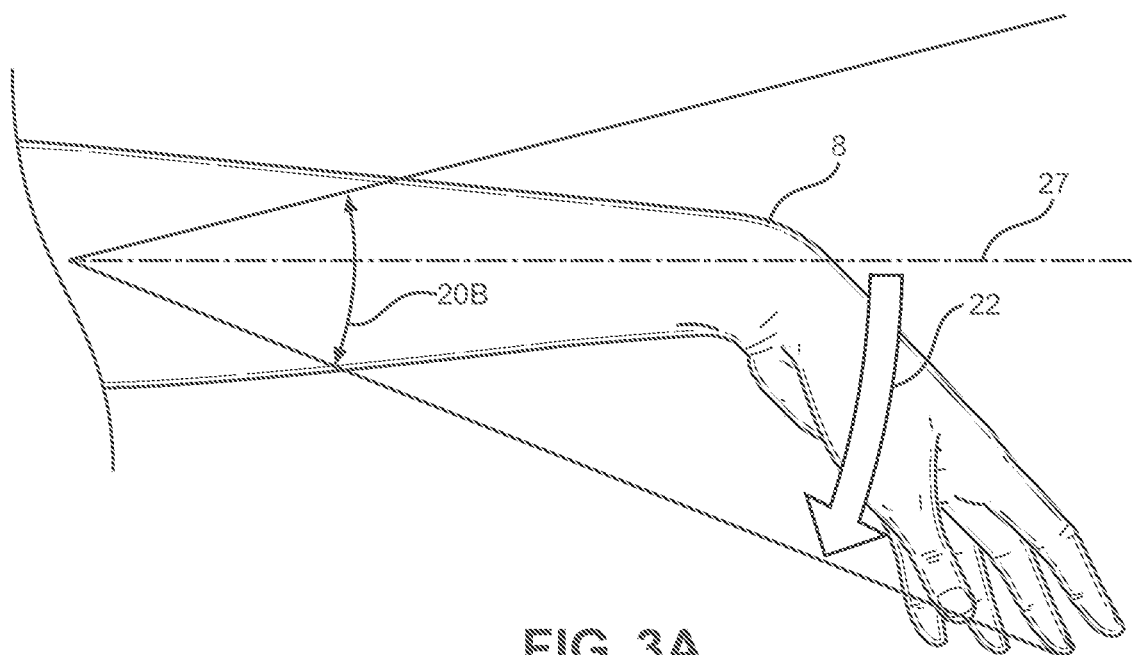
FIG. 3A is a range of motion diagram of the predetermined orientation 20B of a user's body during positioning of a wrist of a user between 0-85 degrees of flexion.
Figure 3B:
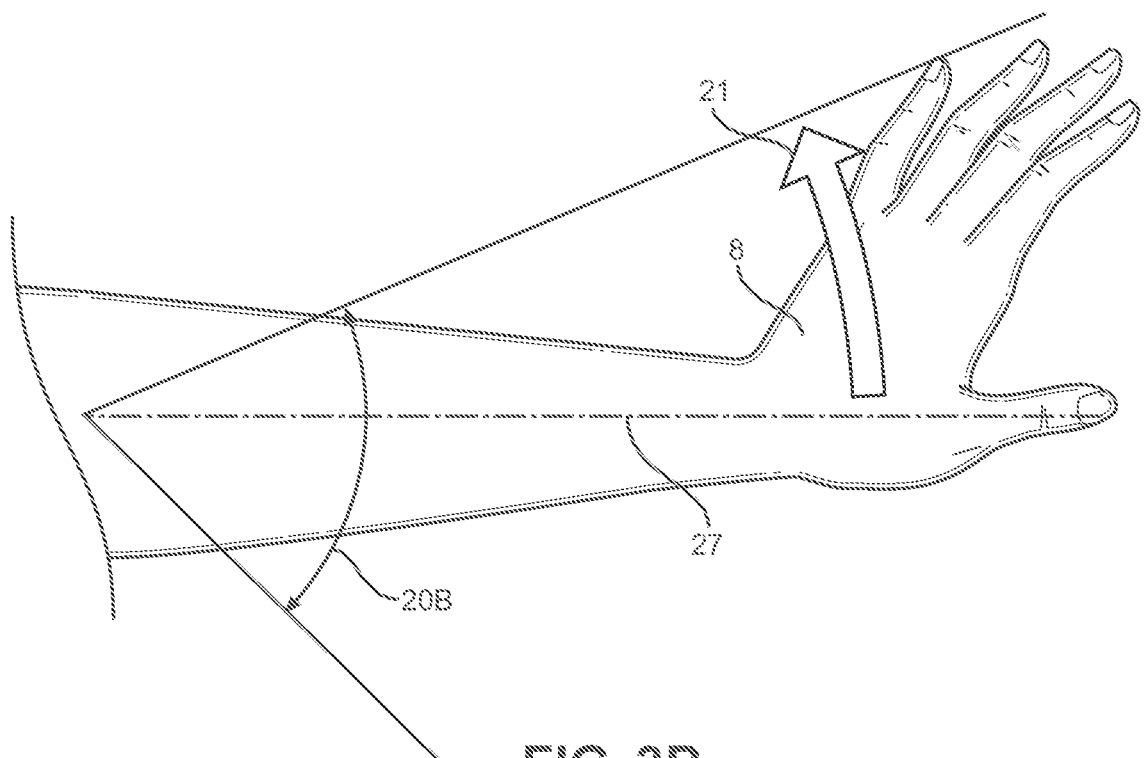
FIG. 3B is a range of motion diagram of the predetermined orientation 20B of a user's body during positioning of a wrist of a user between 0-50 degrees of extension.

In the next step of the first embodiment is to position a user's body to another predetermined orientation 20B simultaneously with the aforementioned predetermined orientation 20A. FIGS. 3A and 3B show the predetermined orientation 20B of a user's body during positioning of at least one wrist 8 of a user between 0-50 degrees of extension 21 (FIG. 3B) or between 0-85 degrees of flexion 22 (FIG. 3A). It is within the scope of this invention for flexion to include the movement of bending the palm down towards the wrist. It is within the scope of this invention for extension to include the movement of raising the back of the hand. It is also within the scope of this invention for predetermined orientation 20B of a user's body having positioning of at least one wrist between 0-45 degrees of extension or between 0-60 degrees of flexion.

Figures 4A, 4B:
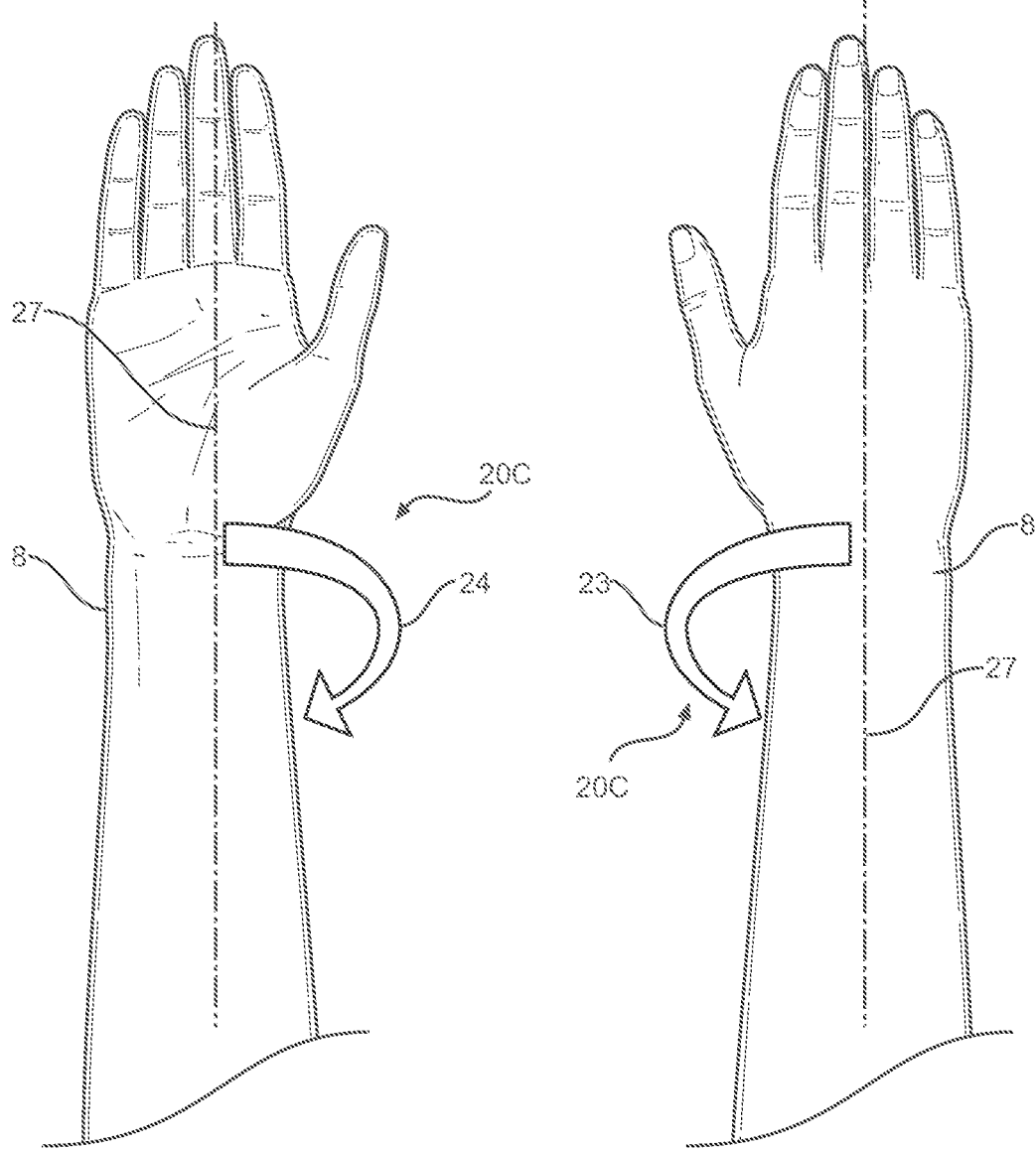
FIG. 4A is a range of motion diagram of the predetermined orientation 20C of a user's body during positioning of a wrist of a user between 0-88 degrees of supination.
FIG. 4B is a range of motion diagram of the predetermined orientation 20C of a user's body during positioning of at least one wrist of a user between 0-88 degrees of pronation.

In the next step of the first embodiment is to orient a user's body to another predetermined orientation 20C simultaneously with predetermined orientations 20A and 20B. FIGS. 4A and 4B show the predetermined orientation 20C of a user's body during positioning of at least one wrist 8 of a user between 0-88 degrees of pronation 23 (FIG. 4B) or between 0-88 degrees of supination 24 (FIG. 4A). It is within the scope of this invention for supination to include the movement of rotating the forearm into a palm up position. It is within the scope of this invention for pronation to include the movement of rotating the forearm into a palm down position. It is also within the scope of this invention for predetermined orientation 20C of a user's body having positioning of at least one wrist 8 between 0-80 degrees of wrist pronation or between 0-80 degrees of wrist supination.

In the next step of the first embodiment is to orient a user's body to a predetermined orientation 20D simultaneously with predetermined orientations 20A 20B, and 20C. FIGS. 5A and 5B show the predetermined orientation 20D of a user's body during positioning of at least one wrist 8 of a user between 0-28 degrees of ulnar deviation 25 (FIG. 5A) or between 0-18 degrees of radial deviation 26 (FIG. 5B). It is within the scope of this invention for at least one wrist 8 of a user to be oriented in predetermined orientation 20D between 28 degrees of ulnar deviation and 18 degrees of radial deviation. FIGS. 3A, 3B, 4A, 4B, 5A, and 5B show that at 0 degrees 27, user's wrist 8 positioning is straight or in a locked orientation. It is within the scope of this invention for ulnar deviation to include the range of motion in which a user's fingers bend in the direction of the ulna bone in the forearm.

Figure 6:
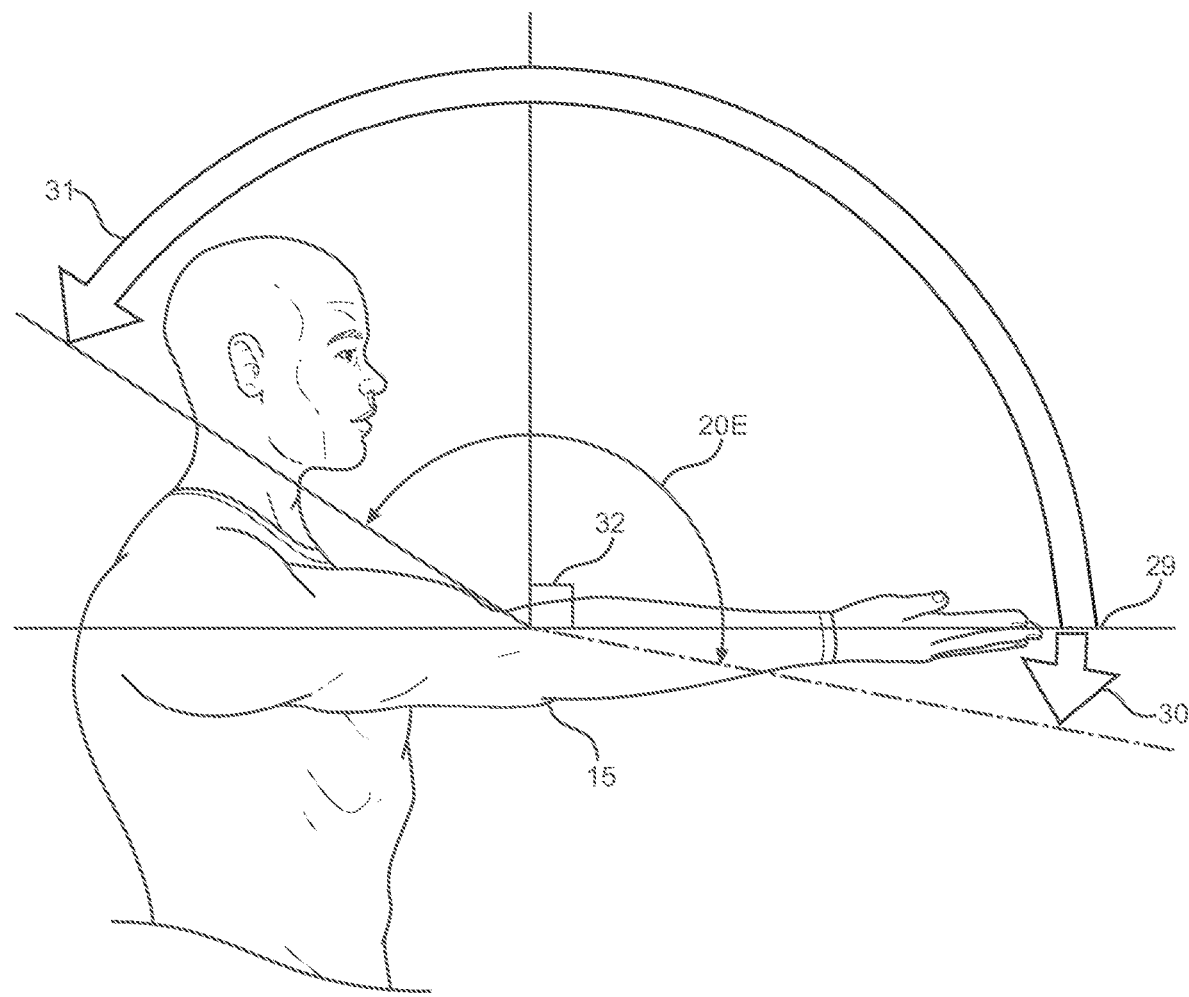
FIG. 6 is a range of motion diagram of the predetermined orientation 20E of a user's body during positioning of an elbow of a user between 0--3 degrees of hyperextension or between 0-130 degrees of flexion.

In the next step of the first embodiment is to orient a user's body to a predetermined orientation 20E simultaneously with predetermined orientations 20A 20B, 20C and 20D. FIG. 6 illustrates the predetermined orientation 20E of a user's body during positioning of at least one elbow 15 of a user between 0--3 degrees of hyperextension 30 or between 0-130 degrees of flexion 31. FIG. 6 show that at 0 degrees 29, user's elbow 15 positioning is straight or in a locked orientation. It is also within the scope of this invention for predetermined orientation 20E of a user's body having positioning of user's elbow 15 to be positioned between 0 degrees of extension 29 and 130 degrees of flexion. It is also within the scope of this invention for predetermined orientation 20E of a user's body having positioning of user's elbow 15 to be positioned between 0 degrees of extension 29 and 125 degrees of flexion. It is also within the scope of this invention for predetermined orientation 20E of a user's body having positioning of user's elbow 15 to be positioned between −3 degrees of hyperextension 30 and 130 degrees of flexion 31.

Figure 7A:
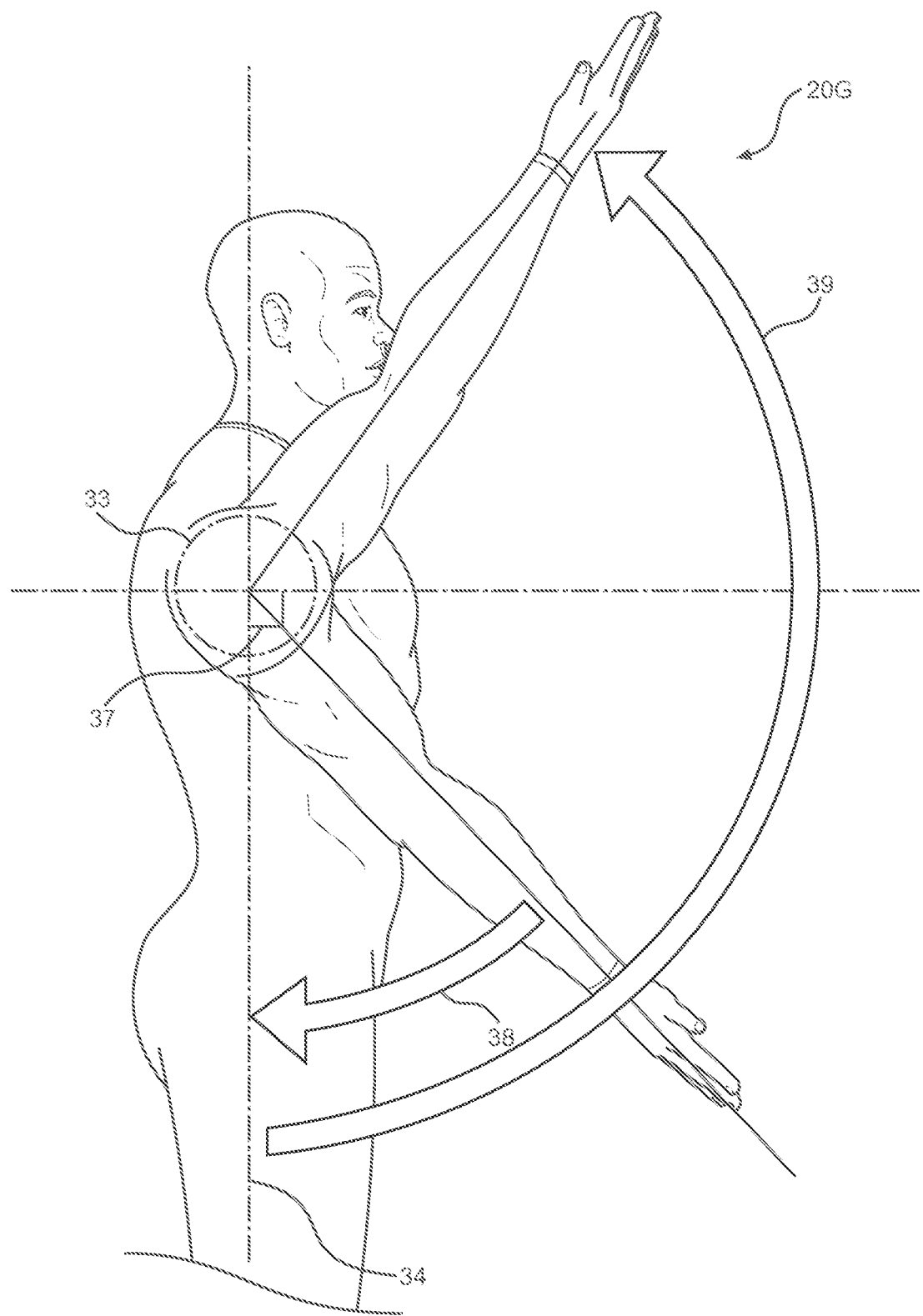
FIG. 7A is a range of motion diagram of the predetermined orientation 20G of a user's body during positioning of a shoulder of a user between 0-145 degrees of shoulder flexion or between 0-58 degrees of extension.
Figure 7B:
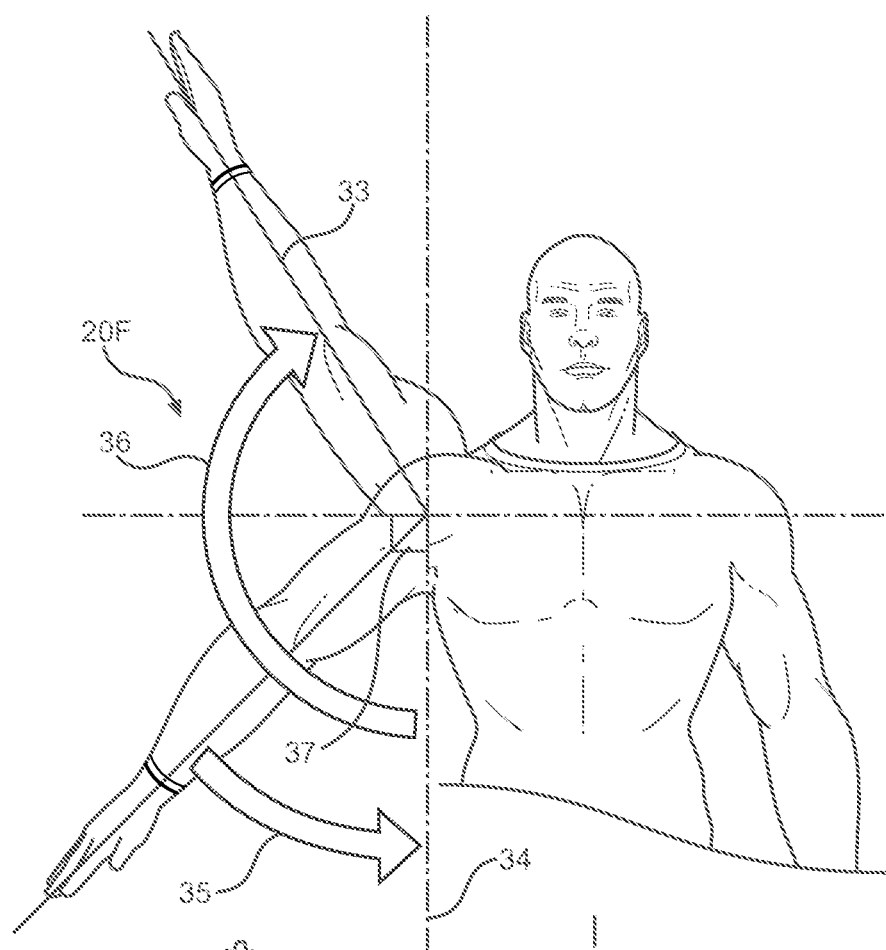
FIG. 7B is a range of motion diagram of the predetermined orientation 20F of a user's body during positioning of a shoulder of a user between 0-145 degrees of shoulder abduction or between 0-45 degrees of shoulder adduction.

In the next step of the first embodiment is to orient a user's body to a predetermined orientation 20F simultaneously with predetermined orientations 20A 20B, 20C, 20D and 20E. FIG. 7B illustrates the predetermined orientation 20F of a user's body during positioning of at least one shoulder 33 of a user between 0-145 degrees of shoulder abduction 36 or between 0-45 degrees of shoulder adduction 35. Lead line 34 illustrates the location of the arm when shoulder 33 is positioned at 0 degrees and at 90 degrees 37.

In the next step of the first embodiment is to orient a user's body to a predetermined orientation 20G simultaneously with predetermined orientations 20A 20B, 20C, 20D, 20E, and 20F. FIG. 7A illustrates the predetermined orientation 20G of a user's body during positioning at least one shoulder 33 of a user between 0-145 degrees of shoulder flexion 39 or between 0-58 degrees of extension 38. Lead line 34 illustrates the location of the arm when shoulder 33 is positioned at 0 degrees and at 90 degrees 37.

Figure 7C:
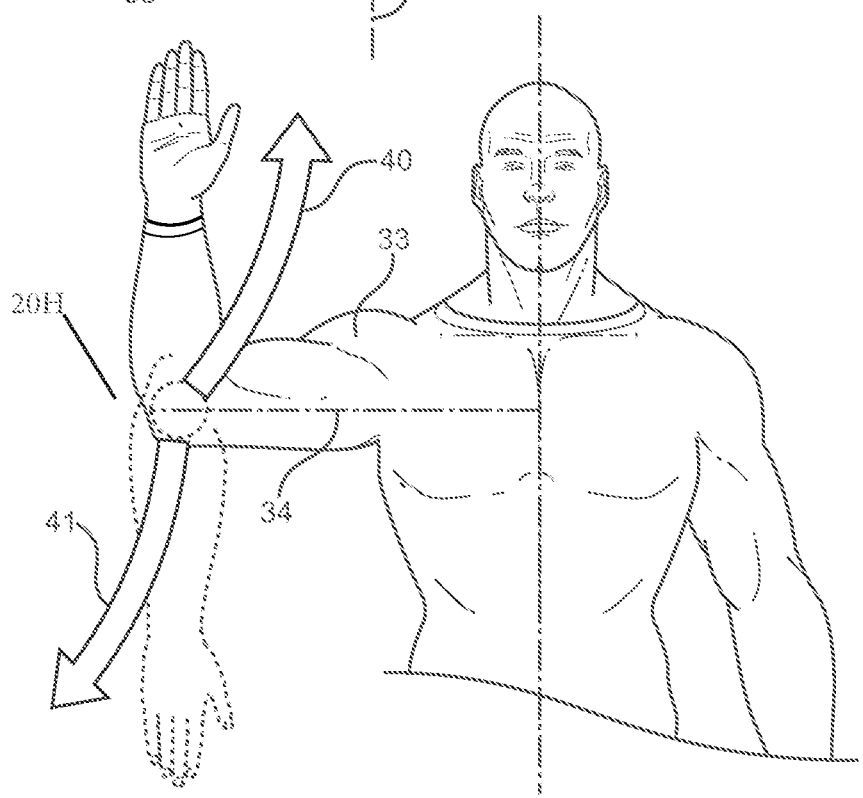
FIG. 7C is a range of motion diagram of the predetermined orientation 20H of a user's body during positioning of a shoulder of a user between 0-85 degrees of external rotation or between 0-50 degrees of internal rotation.

In the next step of the first embodiment is to orient a user's body to a predetermined orientation 20H simultaneously with predetermined orientations 20A 20B, 20C, 20D, 20E, 20F, and 20G. FIG. 7C illustrates the predetermined orientation 20H of a user's body during positioning at least one shoulder of a user between 0-85 degrees of external rotation or between 0-50 degrees of internal rotation.

In the next step of the first embodiment is to apply for example, electrical current from electrical stimulator 1 to said first predetermined location on said user's body, whereby, therapeutic effects 44 (FIG. 8) are experienced at a first predetermined location 14A and 14B and at a second predetermined location 42.

It is within the scope of the aforementioned first embodiment of the method of stimulation of a body of a user for therapeutic effects 44 to provide a garment being sleeve 5 (FIG. 1). First predetermined location 14A on the user's body is at least a portion of an arm. The sleeve receives at least a portion of an arm of the user. Alternatively, the first predetermined location on the user's body is at least a portion of a finger. A sleeve or a glove can receive at least a portion of a finger or a plurality of fingers of a user. Additionally, the garment can be a glove receiving at least one hand or a plurality of hands of a user. Further, the garment may be a pad. The first predetermined location on the user's body can be at least a portion of a shoulder of a user. It is within the scope of this invention for FIG. 8 as well as all embodiments and all Figures for garment 4 to be configured to emit a stimulation 45 including, but not limited to, electrical current, vibration, light, or laser 45 to the first predetermined location on the user's body. The garment may be pneumatically actuated to constrict 46 (FIG. 8) the first predetermined location 14A on a user's body. It is within the scope of this invention for a plurality of stimulation 45 techniques to be employed by the garment. For example, if the first stimulation is electrical stimulation, the second stimulation may be light stimulation.

Figure 8:
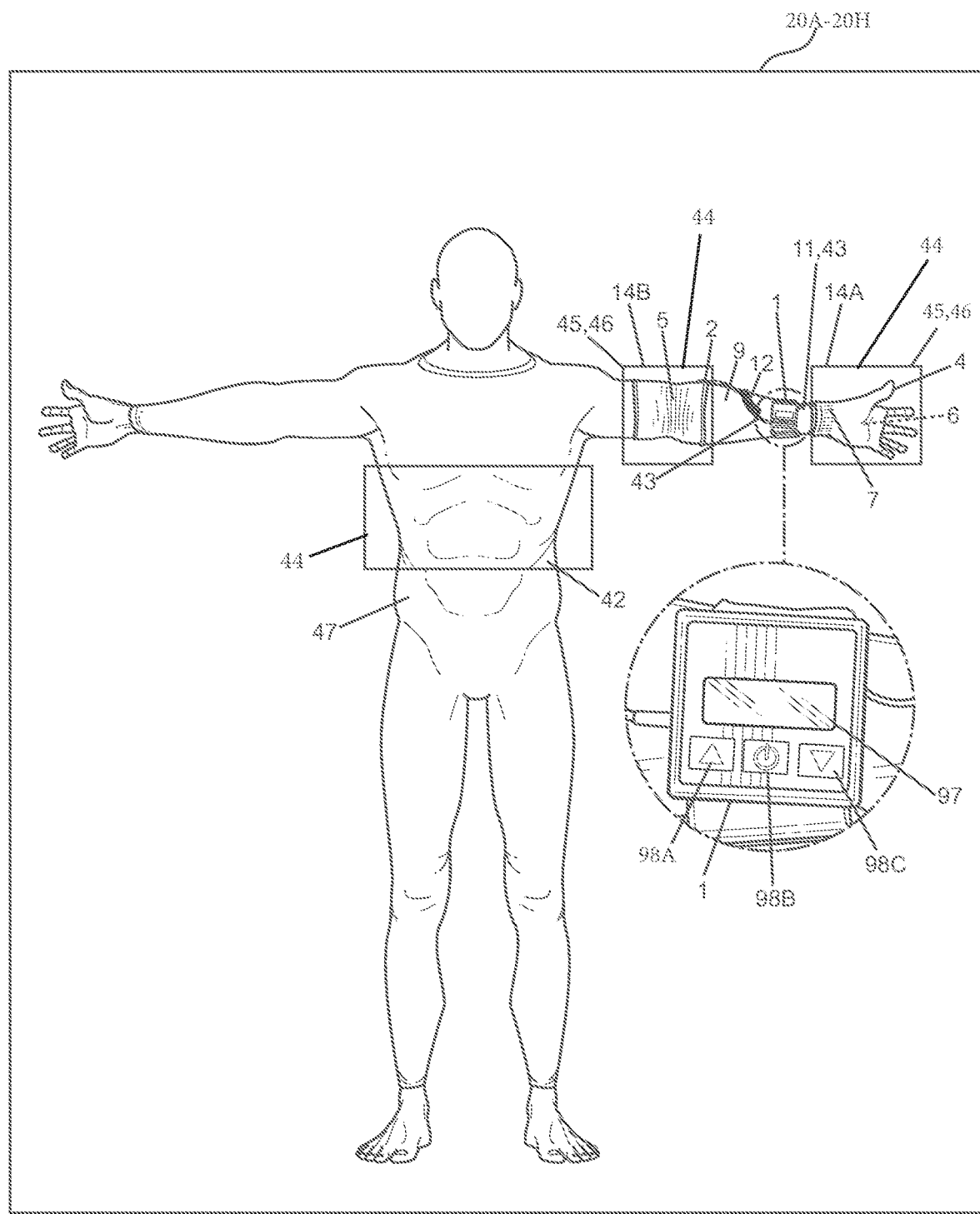
FIG. 8 is a diagram of the novel method of stimulation of the body for therapeutic effects when a user is wearing an electrically conductive glove and an electrically conductive sleeve.

FIG. 8 shows user 47 wearing electrically conductive glove 4 on hand 6. The hand 6 of user 47 is the first predetermined location 14A. Glove 4 is in electrical communication with electrical stimulator 1 and receives electrical current 43 through electrical cord 11. Electrical stimulator 1 is electrically connected to at least one electrode with an electrical cord. First electrical cord 11 has first end 13A located opposite second end 13B. First electrical cord 11 has first end 13A connected to first electrode 2. When stimulated with electric current, for example, an entire area of the forearm or foot or hand, that serves as a map of the entire body and relieves pain everywhere. Furthermore, therapeutic effects 44 are experienced at both the first predetermined location 14 and at second predetermined location 42 when user's body is oriented at a predetermined orientation 20A-20H (FIG. 8). It is within the scope of this invention for predetermined orientations 20A-20W to be within the scope of this invention as shown as this description proceeds.

In a second embodiment of this novel method of stimulation of a body of a user for therapeutic effects, has the steps of providing for example, electrical stimulator 1. Electrical stimulator 1 is electrically connected to an electrode with any electrically conductive element including, but not limited to, a wire, cord, or a cable. As best shown in FIG. 9B, electrical stimulator 1 is electrically connected to a garment. Electrical stimulator 1 is electrically connected to at least one electrode with an electrical cord. First electrical cord 11 has first end 13A located opposite second end 13B. First electrical cord 11 has first end 13A connected to first electrode 2. First electrode 2 is connected to cap 53. First electrical cord 11 has second end 13B connected to electrical stimulator 1. Second electrical cord 12 has first end 10A located opposite second end 10B. Second electrical cord 12 has first end 10A connected to second electrode 3. Second electrode 3 is connected to pad 48. Second electrical cord 12 has second end 10B connected to electrical stimulator 1. It is within the scope of this current invention for a garment to be connected to electrodes 2 and 3 of electrical stimulator 1. A garment includes, but is not limited to, a band, a pad, a sleeve, a wrap, a glove, a sock, a boot, a cap, or a hat. The garment is connected to a first predetermined location on a user's body.

Figure 9A:
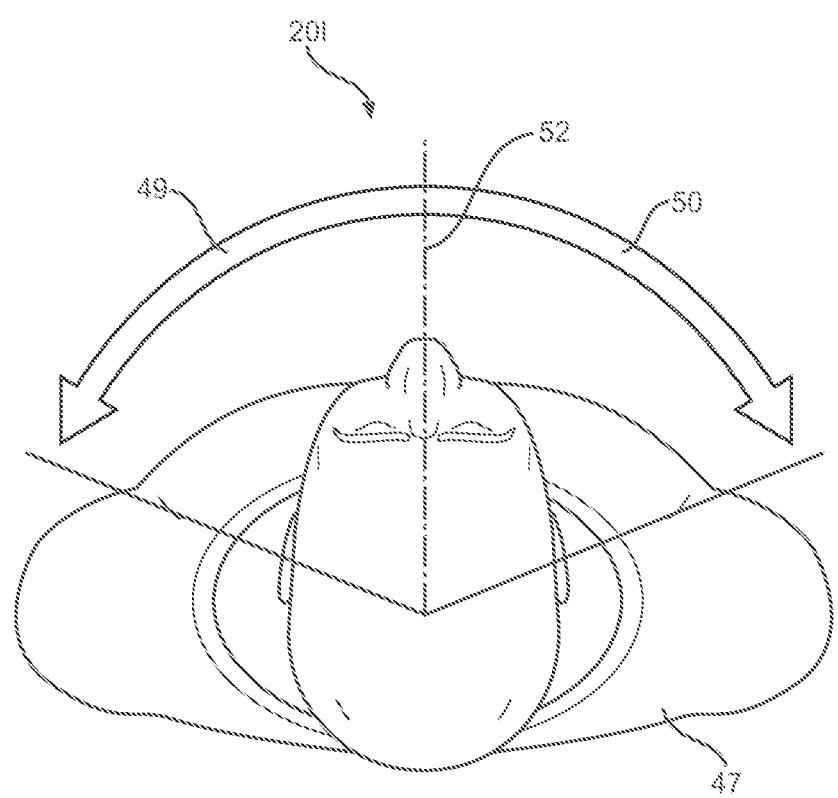
FIG. 9A is a range of motion diagram of the predetermined orientation 20I of a user's body during positioning of a neck of a user between 0-80 degrees of left rotation or between 0-80 degrees of right rotation.
Figure 9B:
FIG. 9B is a range of motion diagram of the predetermined orientation 20J of a user's body during positioning of a neck of a user between 0-65 degrees of flexion or between 0-55 degrees of extension when a user is wearing an electrically conductive cap.
Figure 9C:
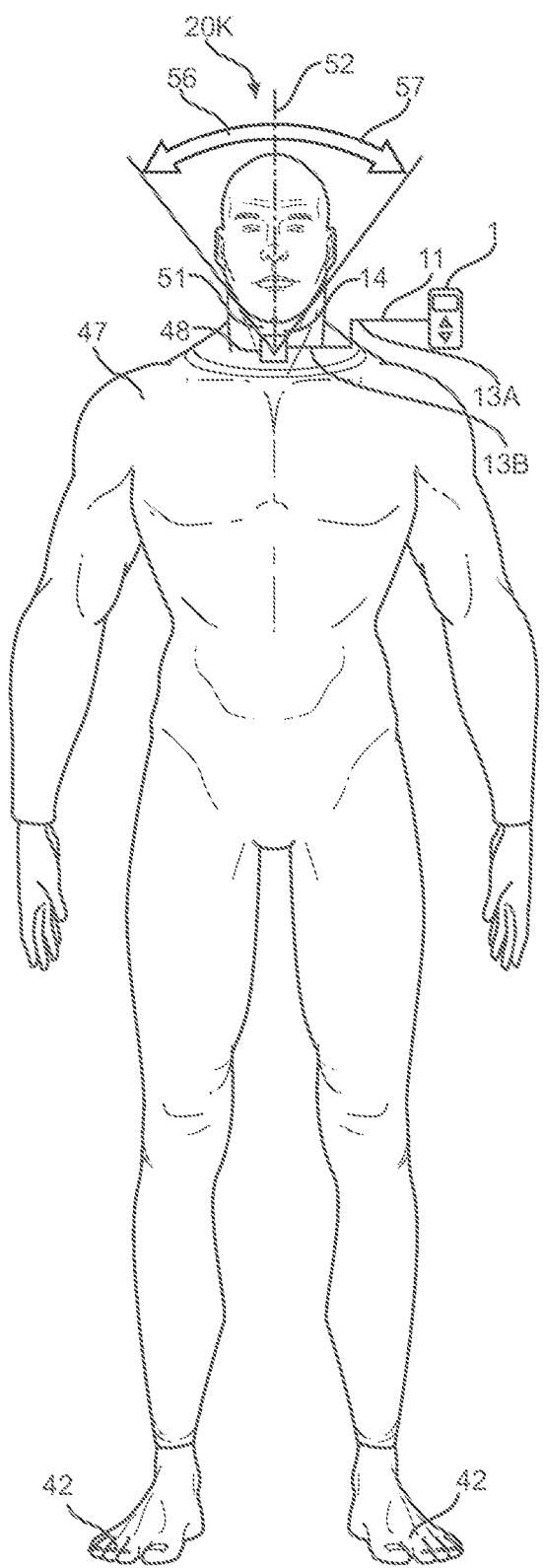
FIG. 9C is a range of motion diagram of the predetermined orientation 20K of a user's body during positioning of a neck of a user between 0-45 degrees of left lateral flexion or between 0-45 degrees of right lateral flexion.

In this second embodiment, FIGS. 9A-9C show when first predetermined location 14 of a user's body is for example, electrically stimulated by electrical stimulator 1 in electrical communication with a garment, therapeutic effects are experienced at both the first predetermined location 14 and at second predetermined location 42. It is within the scope of this second embodiment of the current invention for the second predetermined location 42 to include, but not be limited to, bilateral anterior and posterior aspect of the fingers, toes, thighs, hands, neck, feet, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior cervical spine 51 (FIG. 9B).

In this second embodiment, FIGS. 9A-9C show when first predetermined location 14 of a user's body is for example, electrically stimulated by electrical stimulator 1 in electrical communication with a garment, therapeutic effects are experienced at both the first predetermined location 14 and at second predetermined location 42. It is within the scope of this second embodiment of the current invention for the second predetermined location 42 to include, but not be limited to, bilateral lateral aspect of the fingers, toes, thighs, hands, neck, feet, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the lateral cervical spine 51 (FIG. 9C).

In this second embodiment, first predetermined location 14 of a user's body is for example, electrically stimulated by electrical stimulator 1 in electrical communication with a garment, therapeutic effects are experienced at both the first predetermined location 14 and at second predetermined location 42. It is within the scope of this second embodiment of the current invention for the second predetermined location 42 to include, but not be limited to, bilateral lateral aspect of the fingers, toes, feet, thighs, hands, neck, calves, shins, knees, hips, pelvis/sacrum, abdomen, chest, low back, thoracic spine, shoulders, head, cervical spine, biceps, triceps, elbows, forearm, wrists, and/or gluteus when the first predetermined location 14 is the lateral head.

In this second embodiment, first predetermined location 14 of a user's body is for example, electrically stimulated by electrical stimulator 1 in electrical communication with a garment, therapeutic effects are experienced at both the first predetermined location 14 and at second predetermined location 42. It is within the scope of this second embodiment of the current invention for the second predetermined location 42 to include, but not be limited to, bilateral anterior and posterior aspect of the fingers, toes, feet, calves, shins, thighs, hands, neck, knees, hips, pelvis/sacrum, abdomen, chest, low back, thoracic spine, shoulders, head, cervical spine, biceps, triceps, elbows, forearm, wrists, and/or gluteus when the first predetermined location 14 is the anterior and posterior head.

The next step in the second embodiment is to orient a user's body to a predetermined orientation 20I. FIG. 9A shows the predetermined orientation 20I of a user's body having positioning of neck 51 including, but not limited to, cervical spine of user 47 between 0-80 degrees of left rotation 49 or between 0-80 degrees of right rotation 50. It is within the scope of this invention for the predetermined orientation 20I of a user's body having positioning of neck, including, but not limited to, cervical spine (not shown) of user 47 between 0-45 degrees of left rotation or between 0-45 degrees of right rotation. It is within the scope of this invention for al embodiments to include any portion of a user's neck to be positioned including, but not limited to, the cervical spine of a user.

In the next step of the second embodiment is to orient a user's body to another predetermined orientation 20J simultaneously with predetermined orientation 20I. FIG. 9B illustrates the predetermined orientation 20J of a user's body during positioning of neck 51 of user 47 between 0-65 degrees of flexion 54 or between 0-55 degrees of extension 55. It is also within the scope of this invention for predetermined orientation 20J of a user's body to include positioning of neck 51 of user 47 between 0-50 degrees of flexion and 0-45 degrees of extension, and 0-45 degrees of lateral flexion.

In the next step of the second embodiment is to orient a user's body to another predetermined orientation 20K simultaneously with predetermined orientations 20I and 20J. FIG. 9C illustrates the predetermined orientation 20K of a user's body during positioning of neck 51 of user 47 between 0-45 degrees of right lateral flexion 56 or between 0-45 degrees of left lateral flexion 57. It is within the scope of this invention for predetermined orientation 20K of a user's body having positioning of neck 51 of user 47 between 0-25 degrees of left or right lateral flexion.

In the next step of the second embodiment, electrical current from electrical stimulator 1 is applied to the first predetermined location 14 on user's 47 body. Pain relief is experienced at both first predetermined location 14 and at second predetermined location 42. First predetermined location 14 on user's 47 body is at least a portion of a cervical spine or neck or at least a portion of their head 58. It is within the scope of this invention for garment to be pad 48 (FIGS. 9B and 9C) or cap 53 (FIG. 9B). It is within the scope of this invention for a cap to include any garment worn on the head such as a helmet, a hat, a band, or a wrap. The garment can emit a vibration to the first predetermined location on the user's body. The garment may be pneumatically actuated to intermittently constrict the first predetermined location on a user's body.

Figure 10A:
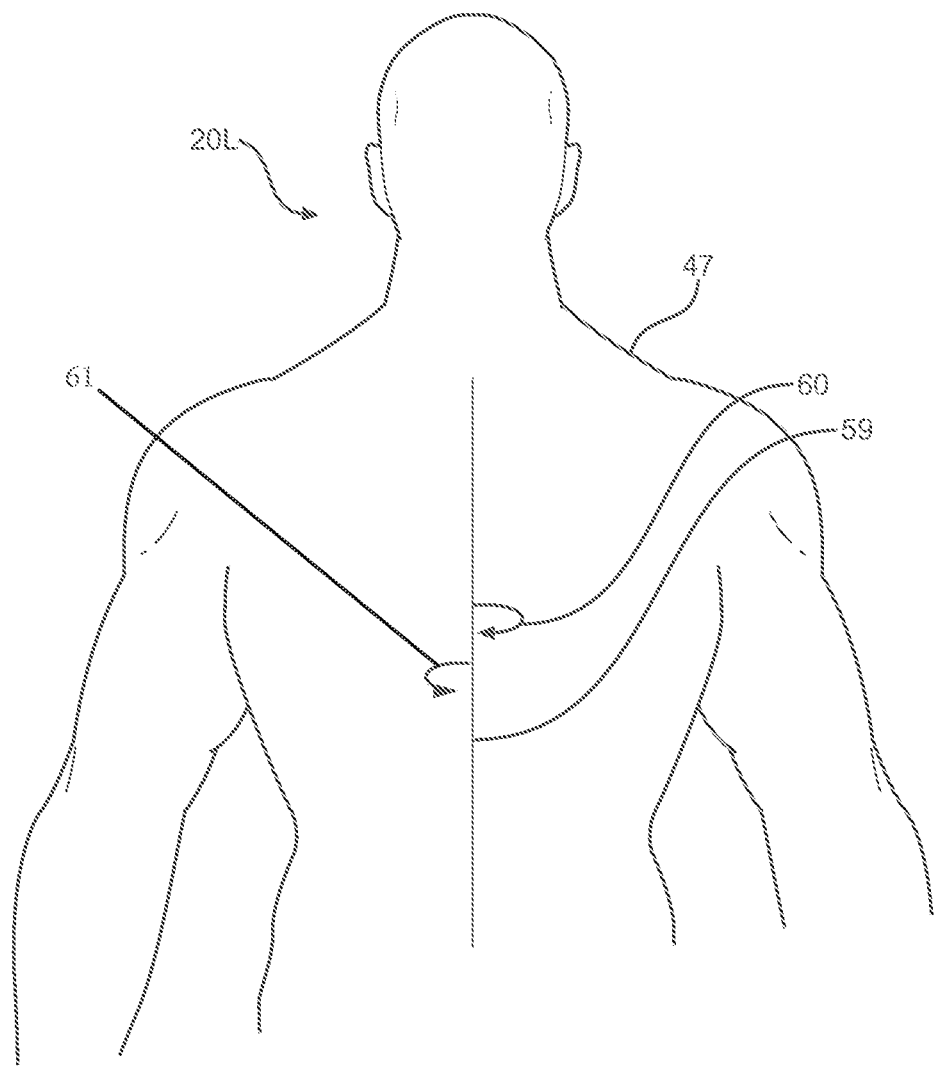
FIG. 10A is a range of motion diagram of the predetermined orientation 20L of a user's body during positioning of a thoracic spine of a user between 0-50 degrees of right rotation and left rotation.
Figure 10D:
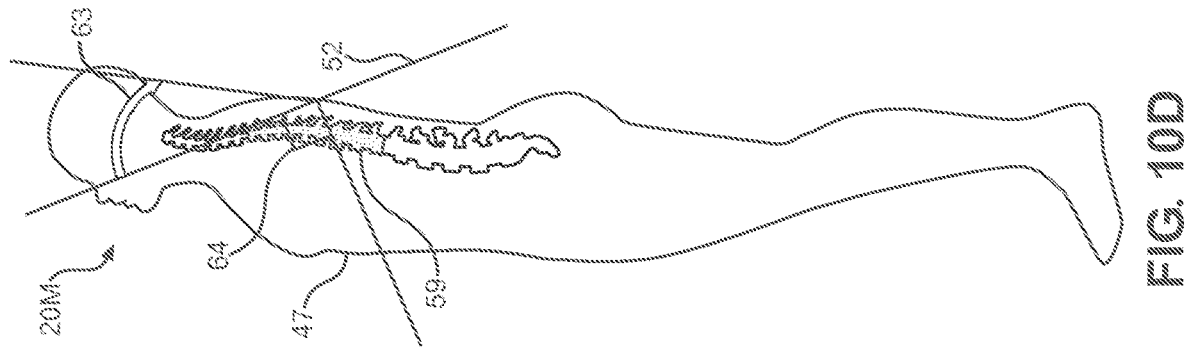
FIG. 10D is a range of motion diagram of the predetermined orientation 20M of a user's body during positioning of a thoracic spine of a user between 0-45 degrees of extension.
Figure 10C:
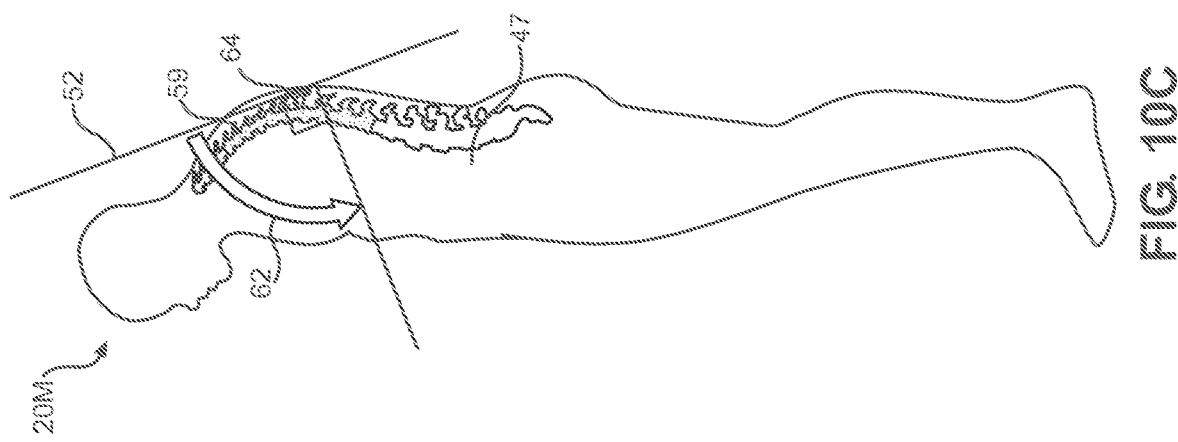
FIG. 10C is a range of motion diagram of the predetermined orientation 20M of a user's body during positioning of a thoracic spine of a user between 0-90 degrees of flexion.
Figure 10B:
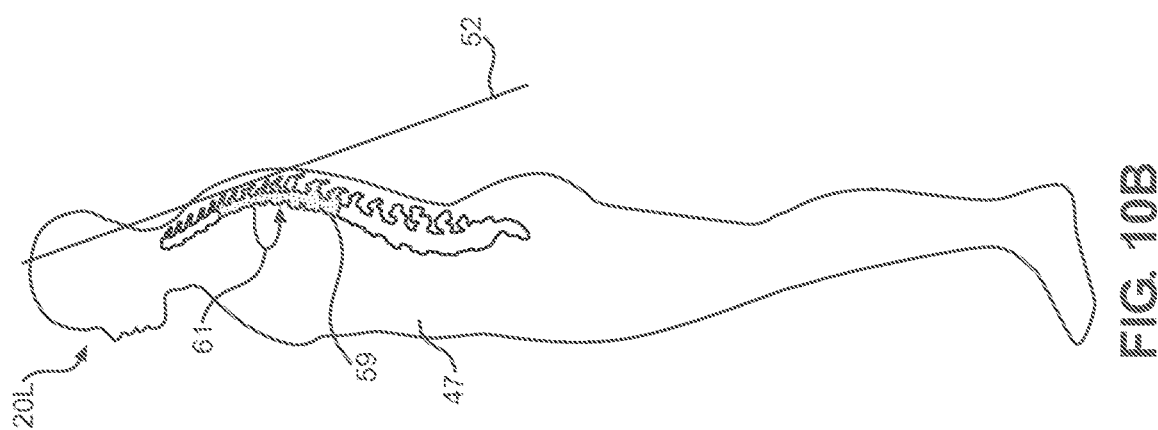
FIG. 10B is a range of motion diagram of the predetermined orientation 20L of a user's body during positioning of a thoracic spine of a user between 0-50 degrees of left rotation.

In another step in the second embodiment is to orient a user's body to a predetermined orientation 20L simultaneously with predetermined orientations 20I, 20J, and 20K. FIGS. 10A and 10B illustrate the predetermined orientation 20L of a user's 47 body having positioning of thoracic spine 59 of user 47 between 0-50 degrees of right rotation 60 (FIG. 10A) or between 0-50 degrees of left rotation 61 (FIG. 10B). It is within the scope of this invention for the second embodiment to include positioning of thoracic spine 59 between 0-35 degrees of rotation, 0-50 degrees of flexion, 0-35 degrees of extension, and 0-30 degrees of lateral flexion.

In another step in the second embodiment is to orient a user's body to a predetermined orientation 20M simultaneously with predetermined orientations 20I, 20J, 20K, and 20L. FIGS. 10C and 10D depict the predetermined orientation 20M of a user's 47 body having positioning of thoracic spine 59 of user 47 between 0-90 degrees of flexion 62 (FIG. 10C) or between 0-45 degrees of extension 63 (FIG. 10D). It is within the scope of this invention for the predetermined orientation 20M of a user's 47 body having positioning of thoracic spine 59 of user 47 between 0-50 degrees of flexion or 0-35 degrees of extension.

Figure 11A:
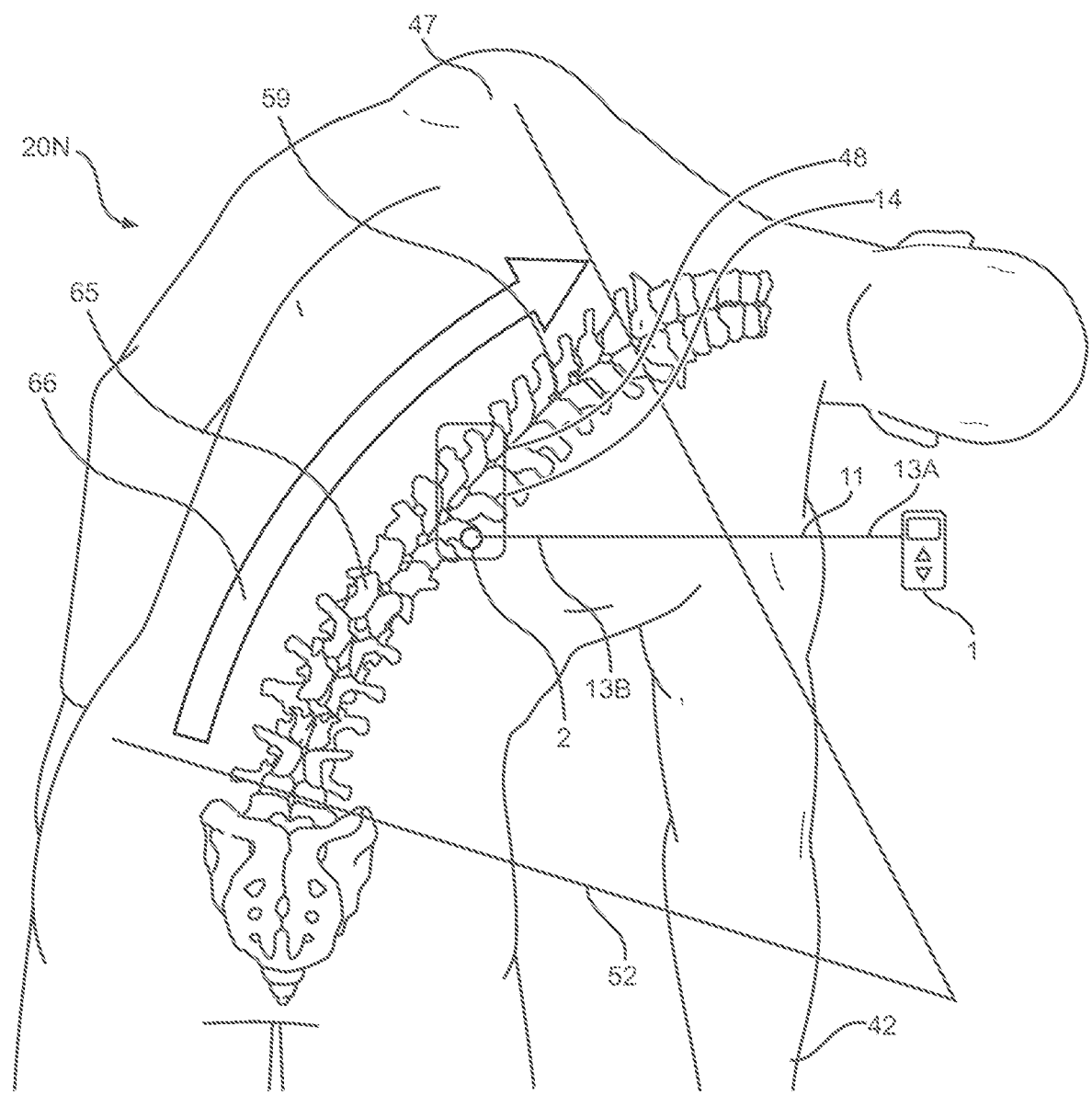
FIG. 11A is a range of motion diagram of the predetermined orientation 20N of a user's body during positioning of a thoracic spine of a user between 0-40 degrees of right lateral flexion.
Figure 11B:
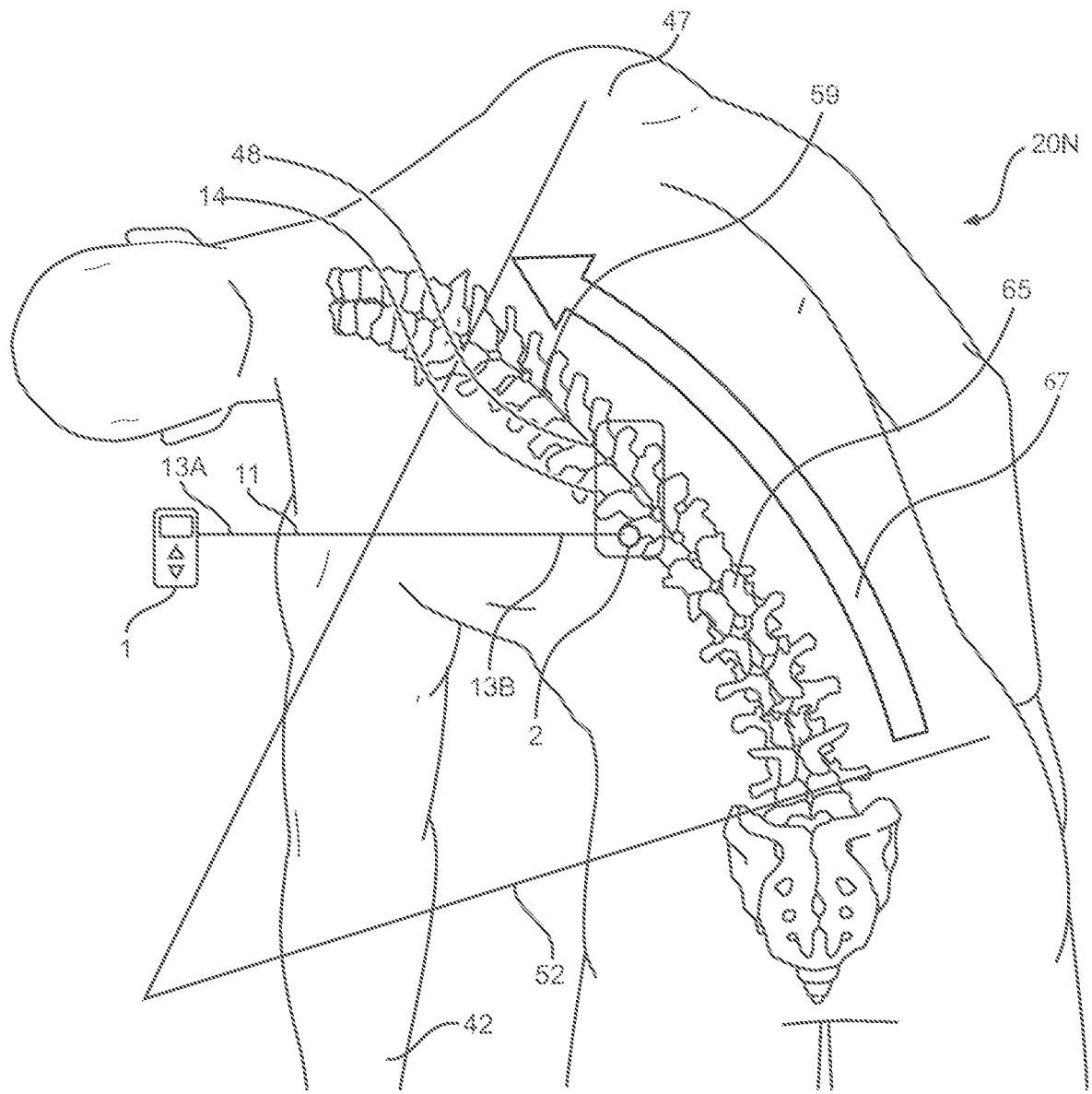
FIG. 11B is a range of motion diagram of the predetermined orientation 20N of a user's body during positioning of a thoracic spine of a user between 0-40 degrees of left lateral flexion.

In another step in the second embodiment is to orient a user's body to another predetermined orientation 20N simultaneously with predetermined orientations 20I, 20J, 20K, 20L, and 20M. FIGS. 11A and 11B depict the predetermined orientation 20N of a user's 47 body having positioning of thoracic spine 59 of user 47 between 0-40 degrees of right lateral flexion 66 (FIG. 11A) or between 0-40 degrees of left lateral flexion 67 (FIG. 11B).

In this second embodiment, FIG. 11A illustrates first predetermined location 14 of a user's body is for example, electrically stimulated by electrical stimulator 1 in electrical communication with a garment being pad 48, therapeutic effects are experienced at both the first predetermined location 14 and at second predetermined location 42 as in the first embodiment. It is within the scope of this second embodiment of the current invention for the second predetermined location 42 to include, but not be limited to, bilateral anterior and posterior aspect of the fingers, toes, thighs, hands, neck, feet, calves, shins, knees, hips, pelvis/sacrum, abdomen, chest, low back, thoracic spine, shoulders, head, neck, biceps, triceps, elbows, forearm, wrists, and/or gluteus when the first predetermined location 14 is the anterior and posterior thoracic. It is within the scope of this invention for the first predetermined location on the user's body to be at least a portion of a spine. Electrical stimulator 1 is electrically connected to a garment being pad 48. Electrical stimulator 1 is electrically connected to at least one electrode with an electrical cord. First electrical cord 11 has first end 13A located opposite second end 13B. First electrical cord 11 has first end 13A connected to first electrode 2. First electrode 2 is connected to pad 48. First electrical cord 11 has second end 13B connected to electrical stimulator 1.

In this second embodiment, first predetermined location 14 of a user's body is for example, electrically stimulated by electrical stimulator 1 in electrical communication with a garment, therapeutic effects are experienced at both the first predetermined location 14 and at second predetermined location 42 of the first embodiment. It is within the scope of this second embodiment of the current invention for the second predetermined location 42 to include, but not be limited to, bilateral medial and lateral aspect of the fingers, toes, feet, thighs, hands, neck, calves, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral thoracic.

Figure 12A:
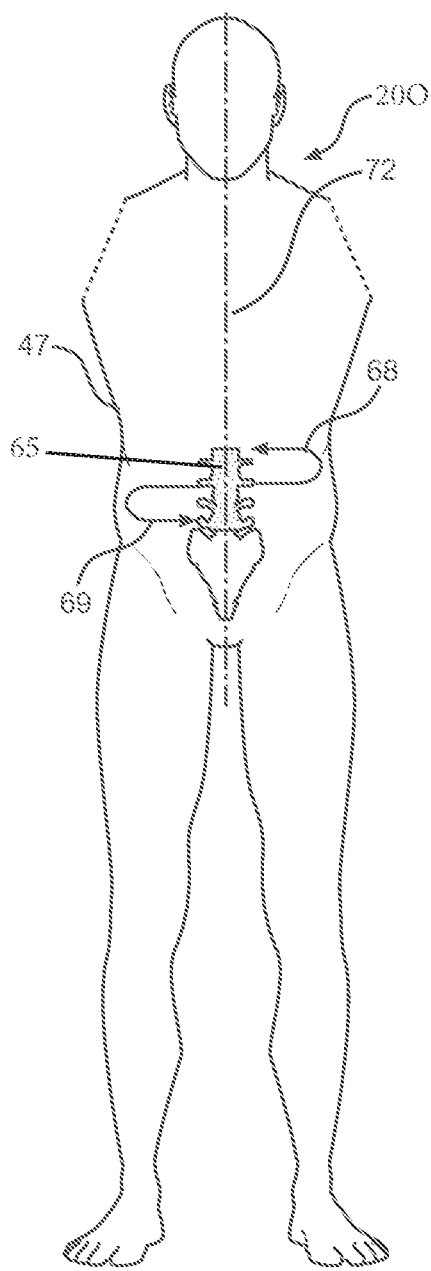
FIG. 12A is a range of motion diagram of the predetermined orientation 20O of a user's body having positioning of lumbar spine of a user between 0-55 degrees of right rotation or between 0-55 degrees of left rotation.

In another step in the second embodiment as illustrated in FIG. 12A, is to orient a user's body to a predetermined orientation 20O simultaneously with predetermined orientations 20I, 20J, 20K, 20L, 20M, and 20N. FIG. 12A depicts the predetermined orientation 20O of a user's 47 body having positioning of lumbar spine 65 of user 47 between 0-55 degrees of right rotation 68 or between 0-55 degrees of left rotation 69. It is also within the scope of this invention for the predetermined orientation 20O of a user's 47 body having positioning of lumbar spine 65 of user 47 between 0-35 degrees of rotation.

Figure 12B:
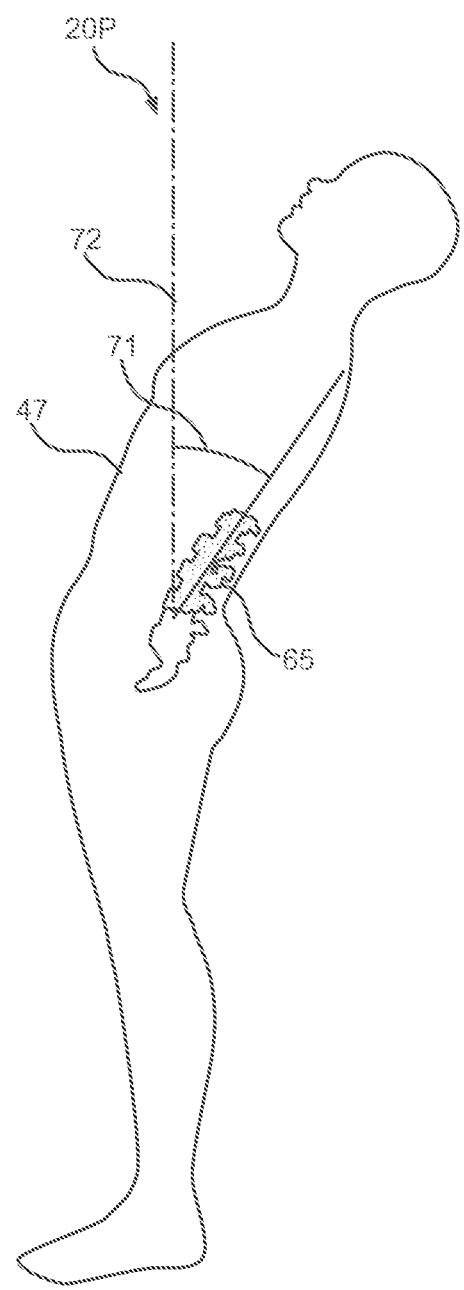
FIG. 12B is a range of motion diagram of the predetermined orientation 20P of a user's body having positioning of lumbar spine of a user between 0-50 degrees of extension.
Figure 12C:
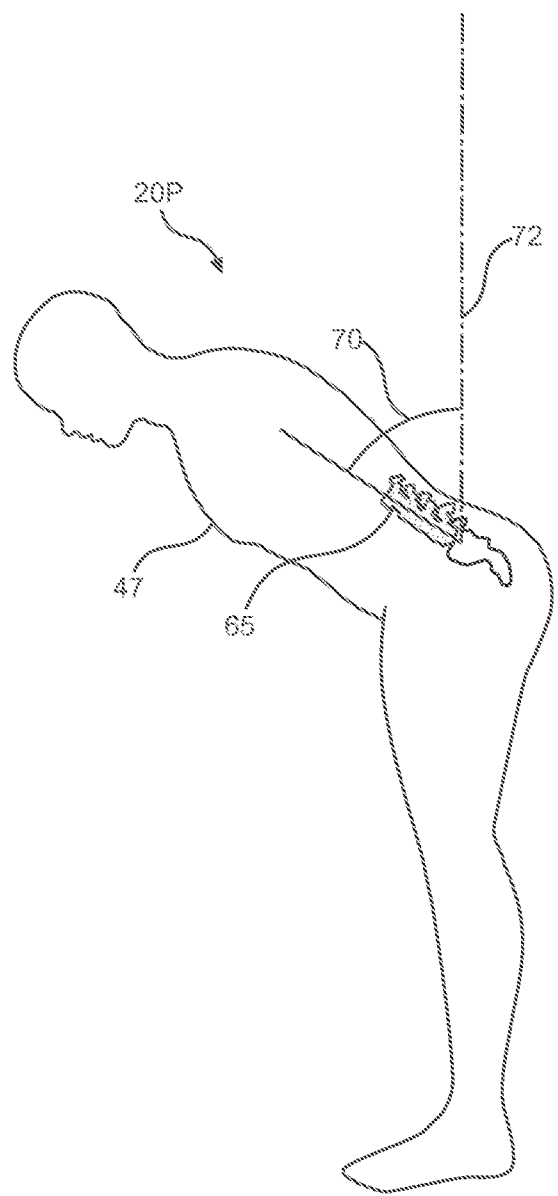
FIG. 12C is a range of motion diagram of the predetermined orientation 20P of a user's body having positioning of lumbar spine of a user between 0-110 degrees of flexion.

In another step in the second embodiment is to orient a user's body to a predetermined orientation 20P simultaneously with predetermined orientations 20I, 20J, 20K, 20L, 20M, 20N, and 20O. FIGS. 12B and 12C illustrate the predetermined orientation 20P of a user's 47 body having positioning of lumbar spine 65 of user 47 between 0-110 degrees of flexion 70 (FIG. 12C) or between 0-50 degrees of extension 71 (FIG. 12B). It is also within the scope of this invention for the predetermined orientation 20P of a user's 47 body having positioning of lumbar spine 65 of user 47 between 0-90 degrees of flexion or between 0-30 degrees of extension.

Figure 12D:
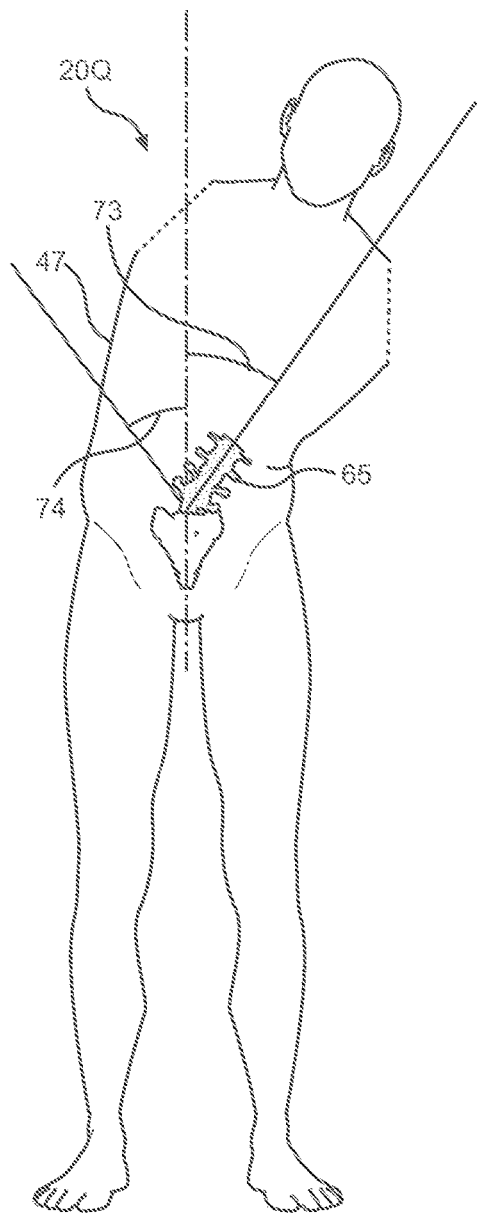
FIG. 12D is a range of motion diagram of the predetermined orientation 20Q of a user's body having positioning of lumbar spine of a user between 0-50 degrees of right lateral flexion or between 0-50 degrees of left lateral flexion.

In another step in the second embodiment is to orient a user's body to a predetermined orientation 20Q simultaneously with predetermined orientations 20I, 20J, 20K, 20L, 20M, 20N, 20O, 20P, and 20Q. FIG. 12D illustrates the predetermined orientation 20Q of a user's 47 body having positioning of lumbar spine 65 of user 47 between 0-50 degrees of right lateral flexion 74 or between 0-50 degrees of left lateral flexion 73. It is also within the scope of this invention for the predetermined orientation 20P of a user's 47 body having positioning of lumbar spine 65 of user 47 between 0-30 degrees of lateral flexion right or left. FIGS. 12A-12D show 0 degrees 72.

In this second embodiment, first predetermined location 14 of a user's body is for example, electrically stimulated by electrical stimulator 1 in electrical communication with a garment, therapeutic effects are experienced at both the first predetermined location 14 and at second predetermined location 42 of the first embodiment. It is within the scope of this second embodiment of the current invention for the second predetermined location 42 to include, but not be limited to, bilateral medial and lateral aspect of the bilateral medial and lateral aspect of the fingers, toes, feet, calves, shins, knees, hips, pelvis/sacrum, abdomen, chest, low back, thoracic spine, shoulders, head, neck, hands, thighs, biceps, triceps, elbows, forearm, wrists, and/or gluteus when the first predetermined location 14 is the medial and lateral lumbar spine/abdomen.

In this second embodiment, first predetermined location 14 of a user's body is for example, electrically stimulated by electrical stimulator 1 in electrical communication with a garment, therapeutic effects are experienced at both the first predetermined location 14 and at second predetermined location 42 of the first embodiment. It is within the scope of this second embodiment of the current invention for the second predetermined location 42 to include, but not be limited to, bilateral anterior and posterior aspect of the fingers, toes, feet, calves, shins, knees, hips, pelvis/sacrum, abdomen, hands, thighs, chest, low back, thoracic spine, shoulders, head, neck, biceps, triceps, elbows, forearm, wrists, and/or gluteus when the first predetermined location 14 is the anterior and posterior lumbar spine/abdomen.

In a third embodiment, first predetermined location 14 of a user's body is for example, electrically stimulated by electrical stimulator 1 in electrical communication with a garment, therapeutic effects are experienced at both the first predetermined location 14 and at second predetermined location 42 of the first embodiment. It is within the scope of this third embodiment of the current invention for the second predetermined location 42 to include, but not be limited to, bilateral anterior and posterior aspect of the fingers, thighs, hands, toes, feet, calves, shins, knees, hips, pelvis/sacrum, abdomen, chest, low back, thoracic spine, shoulders, head, neck, biceps, triceps, elbows, forearm, wrists, and/or gluteus when the first predetermined location 14 is the anterior and posterior pelvis/sacrum/gluets.

Figure 13A:
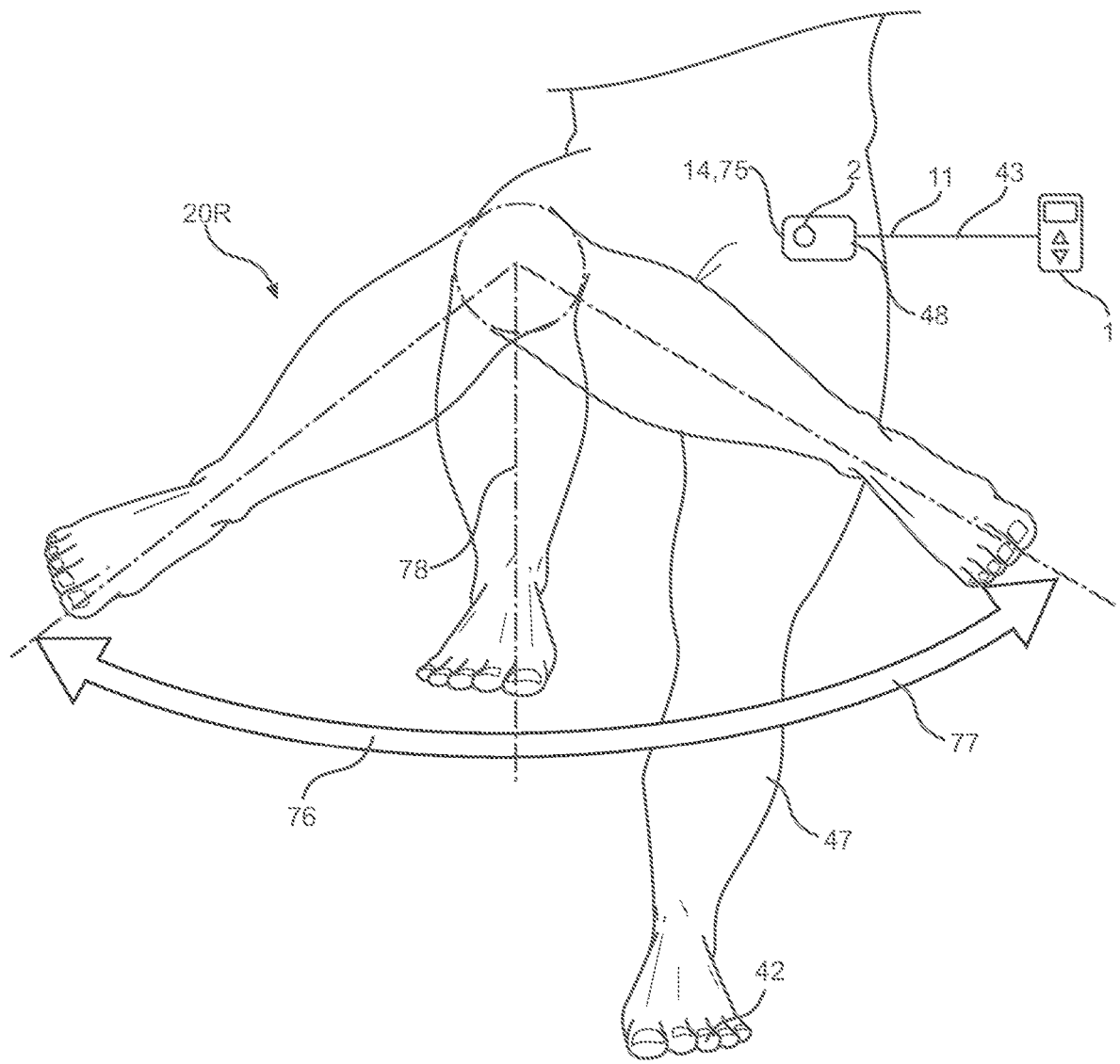
FIG. 13A is a range of motion diagram of the predetermined orientation 20R of a user's body having positioning of hip of a user between 0-38 degrees of internal rotation or between 0-38 degrees of external rotation when a user has an electrically conductive pad connected to a portion of their body.

In a third embodiment, FIG. 13A shows first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this third embodiment of the current invention for the second predetermined location 42 to include, but not be limited to, bilateral medial and lateral aspect of the fingers, hands, thighs, toes, feet, calves, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral pelvis/sacrum/gluets.

Figure 13B:
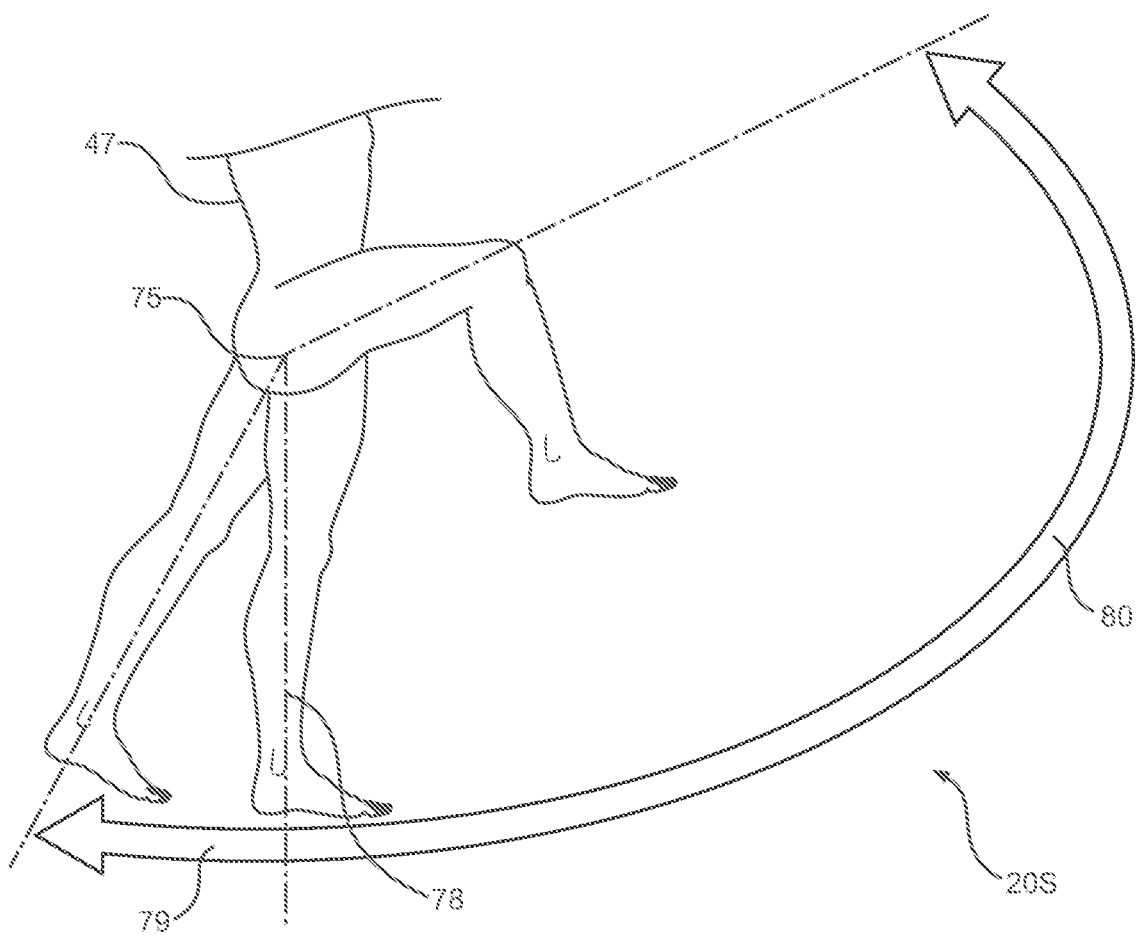
FIG. 13B is a range of motion diagram of the predetermined orientation 20S of a user's body having positioning of hip of a user between 0-40 degrees of extension or between 0-130 degrees of flexion.

In another step in the third embodiment is to orient a user's body to a predetermined orientation 20R simultaneously with predetermined orientations 20L, 20M, 20N, 20O, 20P, and 20Q. FIG. 13A illustrates the predetermined orientation 20R of a user's 47 body having positioning of hip 75 of user 47 between 0-38 degrees of internal rotation 76 or between 0-38 degrees of external rotation 77. It is also within the scope of this invention for the predetermined orientation 20R of a user's 47 body having positioning of hip 75 having internal or external rotation between 0-32 degrees. FIGS. 13A and 13B show 0 degrees 78.

In another step in the third embodiment is to orient a user's body to a predetermined orientation 20S simultaneously with predetermined orientations 20L, 20M, 20N, 20O, 20P, 20Q, and 20R. FIG. 13B illustrates the predetermined orientation 20S of a user's 47 body having positioning of hip 75 of user 47 between 0-40 degrees of extension 79 or between 0-130 degrees of flexion 80. It is also within the scope of this invention for the predetermined orientation 20S of a user's 47 body having positioning of hip 75 having extension between 0-30 degrees or hip flexion between 0-120 degrees.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to, bilateral medial and lateral aspect of the fingers, hands, thighs, toes, feet, calves, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral hamstring/quad.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to bilateral anterior and posterior aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the anterior and posterior hamstring/quad.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to, bilateral anterior and posterior aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the anterior and posterior knee.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to, bilateral medial and lateral aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral knee.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to, bilateral medial and lateral aspect of fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral shin/calf.

In a fourth embodiment, first predetermined location 14 of a user's body is for example, electrically stimulated 43 by electrical stimulator 1 in electrical communication with a garment being pad 48, therapeutic effects are experienced at both the first predetermined location 14 and at second predetermined location 42 of the first embodiment. It is within the scope of this fourth embodiment of the current invention for the second predetermined location 42 to include, but not be limited to, bilateral anterior and posterior aspect of fingers, toes, feet, calves, hands, thighs, shins, knees, hips, pelvis/sacrum, abdomen, chest, low back, thoracic spine, shoulders, head, neck, biceps, triceps, elbows, forearm, wrists, gluteus when the first predetermined location 14 is the anterior and posterior shin/calf.

Figure 14A:
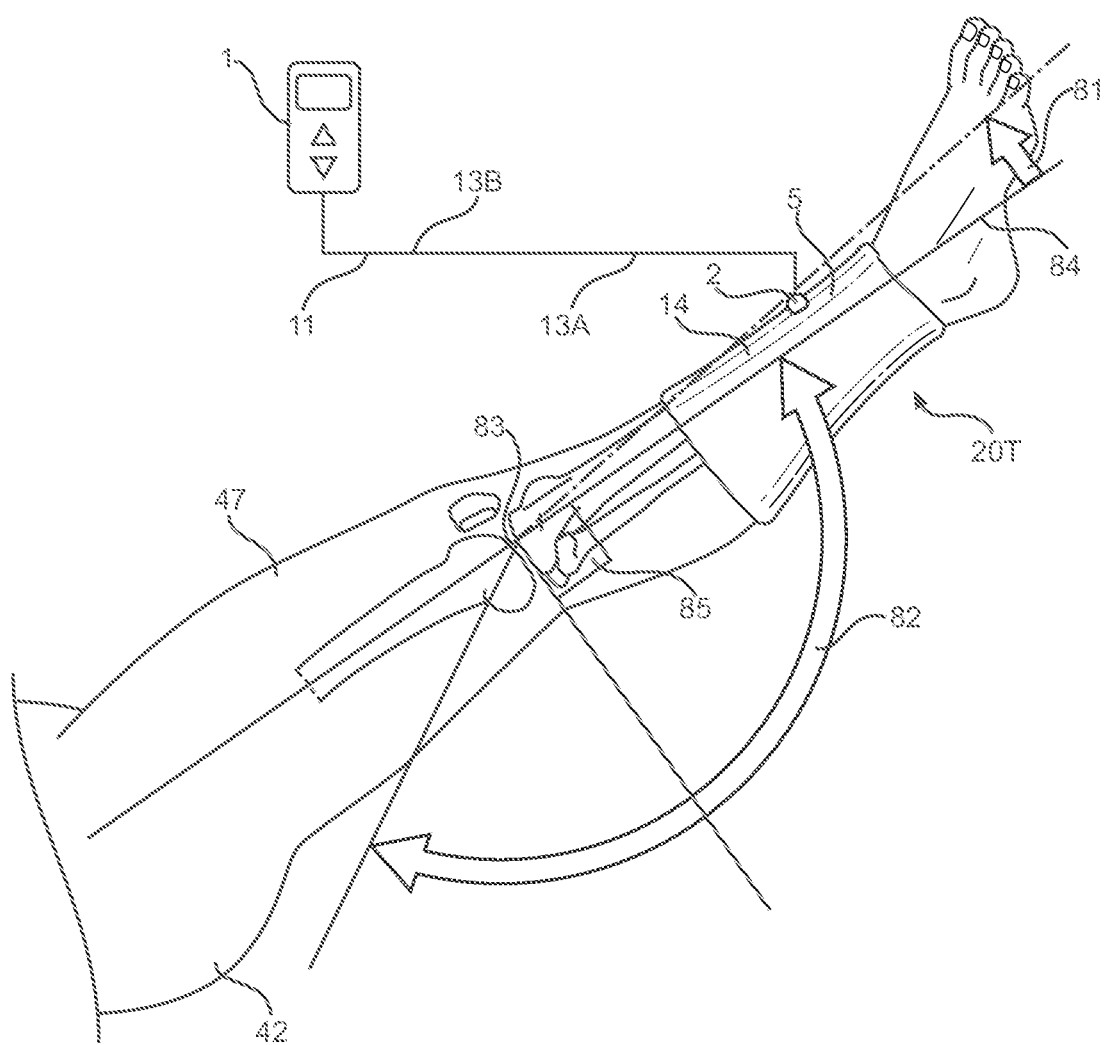
FIG. 14A is a range of motion diagram of the predetermined orientation 20T of a user's body having positioning of a knee of a user between 0--5 degrees of hyperextension or between 0-125 degrees of flexion when a user is wearing an electrically conductive sleeve.

In another step in the fourth embodiment is to is to orient a user's body to a predetermined orientation 20T simultaneously with predetermined orientations 20O, 20P, 20Q, 20R, and 20S. FIG. 14A illustrates the predetermined orientation 20T of a user's 47 body having positioning of knee 83 of user 47 between 0--5 degrees of hyperextension 81 or between 0-125 degrees of flexion 82. It is within the scope of this invention for the knee to be in a locked or straightened position at 0 degrees 84. FIG. 14A shows 90-degree angle 85. User's leg receives electrically conductive sleeve 5. Sleeve 4 is in electrical communication with electrical stimulator 1 and receives electrical current 43 through electrical cord 11. Electrical stimulator 1 is electrically connected to at least one electrode with an electrical cord. First electrical cord 11 has first end 13A located opposite second end 13B. First electrical cord 11 has first end 13A connected to first electrode 2. Therapeutic effects are experienced at both the first predetermined location 14 and at second predetermined location 42.

Figure 14B:
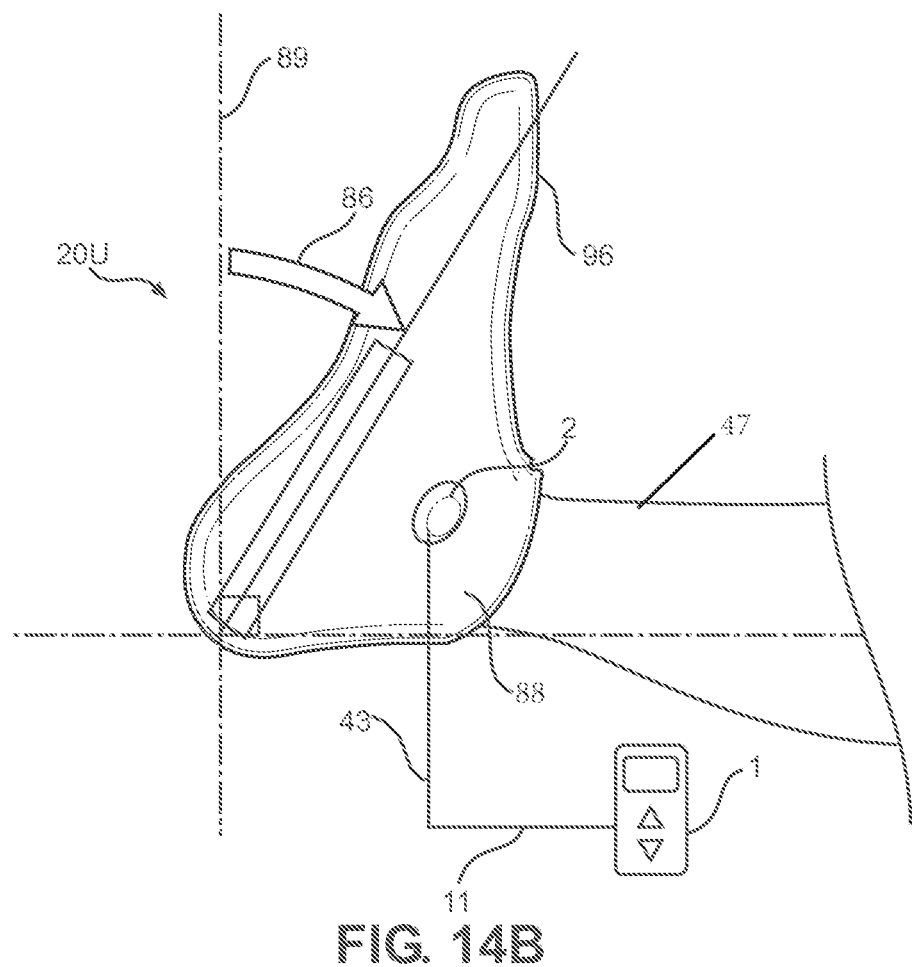
FIG. 14B is a range of motion diagram of the predetermined orientation 20U of a user's body having positioning of ankle of a user between 0-14 degrees of dorsiflexion when a user wears an electrically conductive garment being a sock.
Figure 14C:
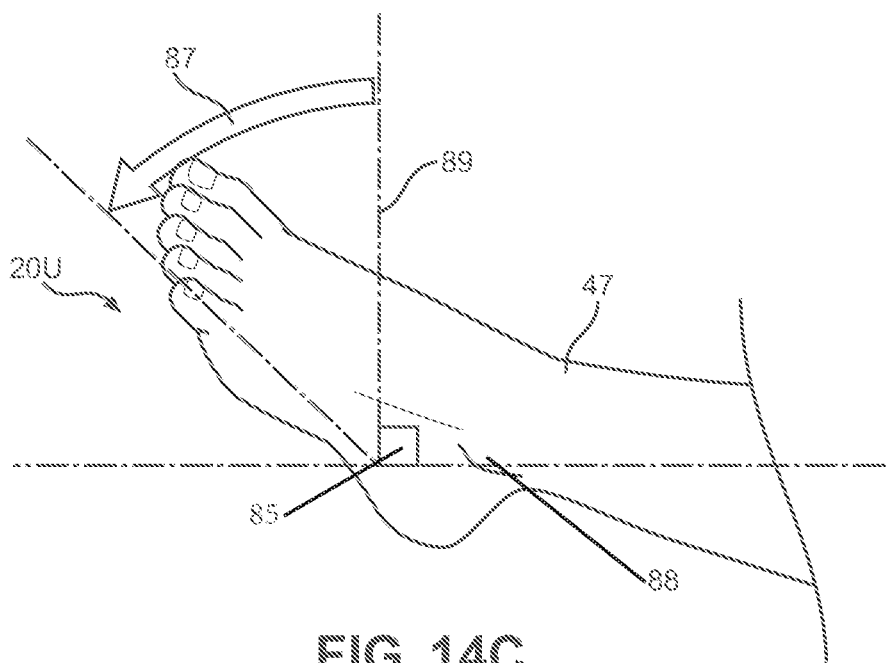
FIG. 14C is a range of motion diagram of the predetermined orientation 20U of a user's body having positioning of ankle of a user between 0-55 degrees of plantar flexion.

In another step in the fourth embodiment is to is to orient a user's body to a predetermined orientation 20U simultaneously with predetermined orientations 20O, 20P, 20Q, 20R, 20S, and 20T. FIGS. 14B and 14C illustrate the predetermined orientation 20U of a user's 47 body having positioning of ankle 88 of user 47 between 0-14 degrees of dorsiflexion 86 (FIG. 14B) or between 0-55 degrees of plantar flexion 87 (FIG. 14C). In an alternate embodiment, ankle dorsiflexion has a range between 0-12 degrees and ankle plantar flexion has a range between 0-55 degrees. 0 degrees 89 is illustrated.

Figure 14D:
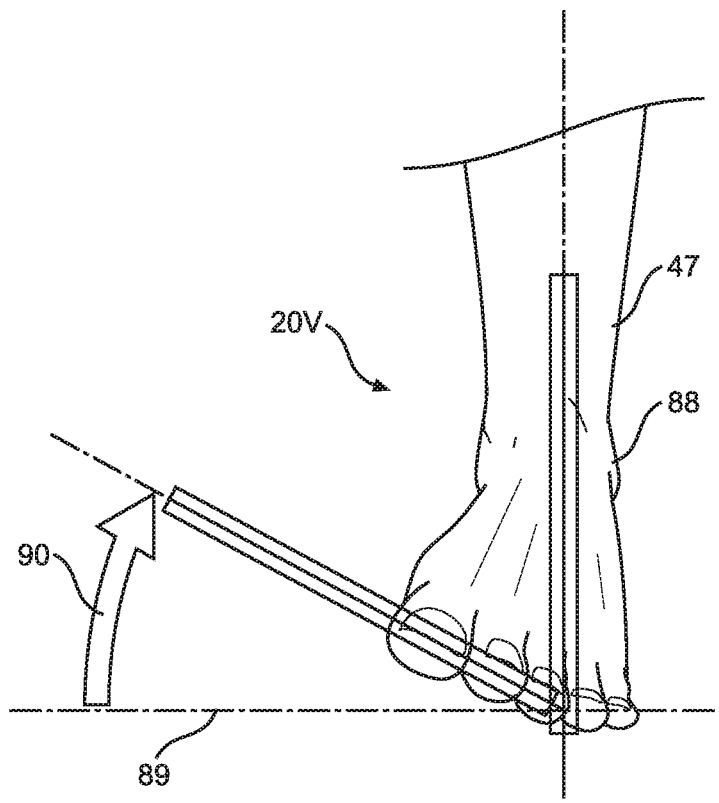
FIG. 14D is a range of motion diagram of the predetermined orientation 20V of a user's body having positioning of an ankle of a user between 0-35 degrees of inversion.
Figure 14E:
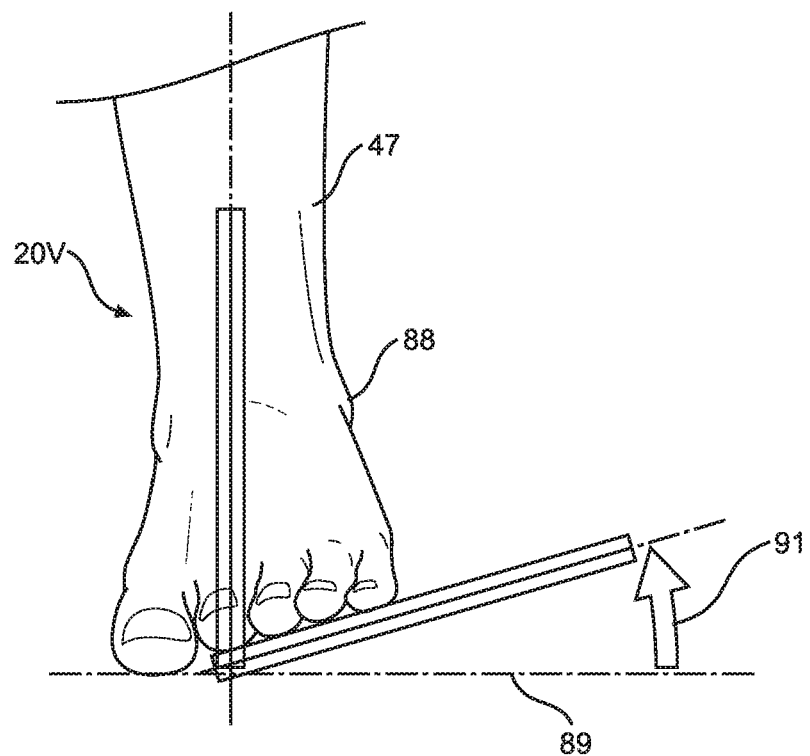
FIG. 14E is a range of motion diagram of the predetermined orientation 20V of a user's body having positioning of an ankle of a user between 0-25 degrees of eversion.

In another step in the fourth embodiment is to is to orient a user's body to a predetermined orientation 20V simultaneously with predetermined orientations 20O, 20P, 20Q, 20R, 20S, 20T, and 20U. FIGS. 14D and 14E illustrate the predetermined orientation 20V of a user's 47 body having positioning of ankle 88 of user 47 between 0-35 degrees of inversion 90 (FIG. 14D) or between 0-25 degrees of eversion 91 (FIG. 14E). 0 degrees 89 is illustrated.

In the fourth embodiment, first predetermined location 14 of a user's body is for example, electrically stimulated 43 by electrical stimulator 1 in electrical communication with a garment being pad 48 of previous embodiments, therapeutic effects are experienced at both the first predetermined location 14 and at second predetermined location 42 of the first embodiment. It is within the scope of this fourth embodiment of the current invention for the second predetermined location 42 to include, but not be limited to, bilateral anterior and posterior aspect of the fingers, toes, feet, calves, shins, hands, thighs, knees, hips, pelvis/sacrum, abdomen, chest, low back, thoracic spine, shoulders, head, neck, biceps, triceps, elbows, forearm, wrists, and/or gluteus when the first predetermined location 14 is the anterior and posterior ankle/foot.

In the fourth embodiment, first predetermined location 14 of a user's body is for example, electrically stimulated 43 by electrical stimulator 1 in electrical communication with a garment being pad 48 of previous embodiments, therapeutic effects are experienced at both the first predetermined location 14 and at second predetermined location 42 of the first embodiment. It is within the scope of this fourth embodiment of the current invention for the second predetermined location 42 to include, but not be limited to, bilateral medial and lateral aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral ankle/foot.

In the fourth embodiment, first predetermined location 14 of a user's body is for example, electrically stimulated 43 by electrical stimulator 1 in electrical communication with a garment being pad 48 of previous embodiments, therapeutic effects are experienced at both the first predetermined location 14 and at second predetermined location 42 of the first embodiment. It is within the scope of this fourth embodiment of the current invention for the second predetermined location 42 to include, but not be limited to, bilateral medial and lateral aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, and/or gluteus when the first predetermined location 14 is the medial and lateral toes.

In the fourth embodiment, first predetermined location 14 of a user's body is for example, electrically stimulated 43 by electrical stimulator 1 in electrical communication with a garment being pad 48 of previous embodiments, therapeutic effects are experienced at both the first predetermined location 14 and at second predetermined location 42 of the first embodiment. It is within the scope of this fourth embodiment of the current invention for the second predetermined location 42 to include, but not be limited to, bilateral anterior and posterior aspect of the fingers, toes, feet, calves, hands, thighs, shins, knees, hips, pelvis/sacrum, abdomen, chest, low back, thoracic spine, shoulders, head, neck, biceps, triceps, elbows, forearm, wrists, gluteus when the first predetermined location 14 is the anterior and posterior toes.

It is within the scope of the fourth embodiment for the garment to be a sleeve. The first predetermined location on the user's body can be at least a portion of a leg. The sleeve receives at least a portion of the leg of the user. It is within the scope of this invention for the MCP joint of the hand to have the following positioning in which adduction and abduction are positioned between a range of 0 degrees to 23 degrees. It is within the scope of this invention for the MTP joint of the foot to have the following positioning in which adduction and abduction are positioned between a range of 0 degrees to 8 degrees. It is within the scope of this invention for the temporomandibular joint, configured for the opening of the mouth between 0 millimeters to 38 millimeters. It is within the scope of this invention for the protrusion of the mandible to be between 0 millimeters and 3 millimeters of protrusion and for the lateral deviation to be between 0 millimeters and 6 millimeters.

Figure 15A:
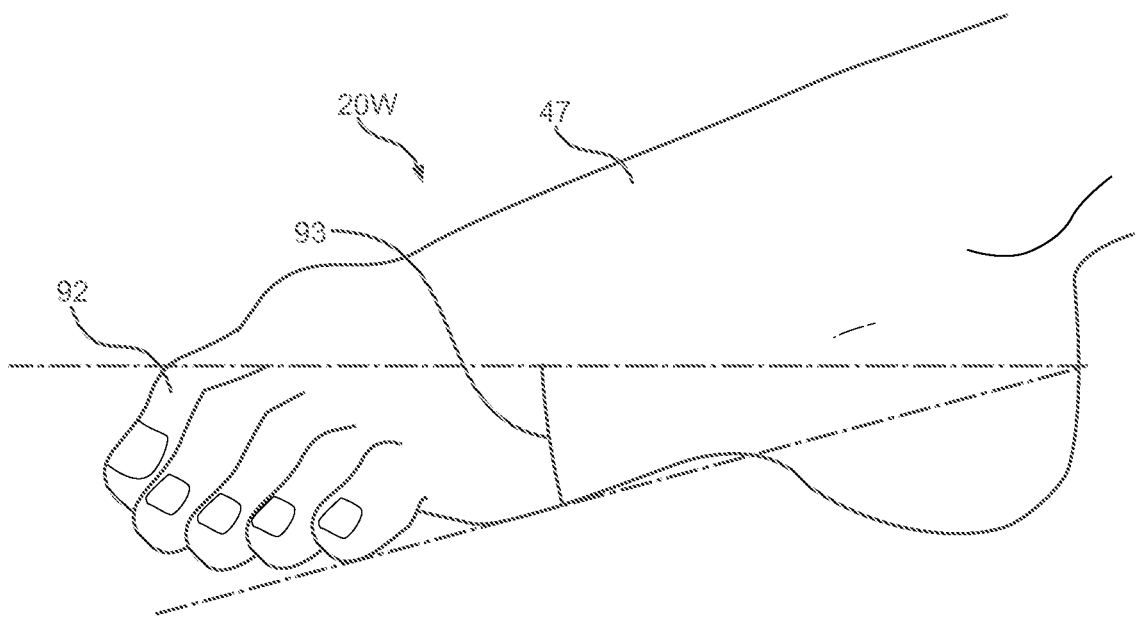
FIG. 15A is a range of motion diagram of the predetermined orientation 20W of a user's body having positioning of at least one toe of a user between 0-45 degrees of flexion; and, FIG. 15B is a range of motion diagram of the predetermined orientation 20W of a user's body having positioning of at least one toe of a user between 0-45 degrees of extension.
Figure 15B:
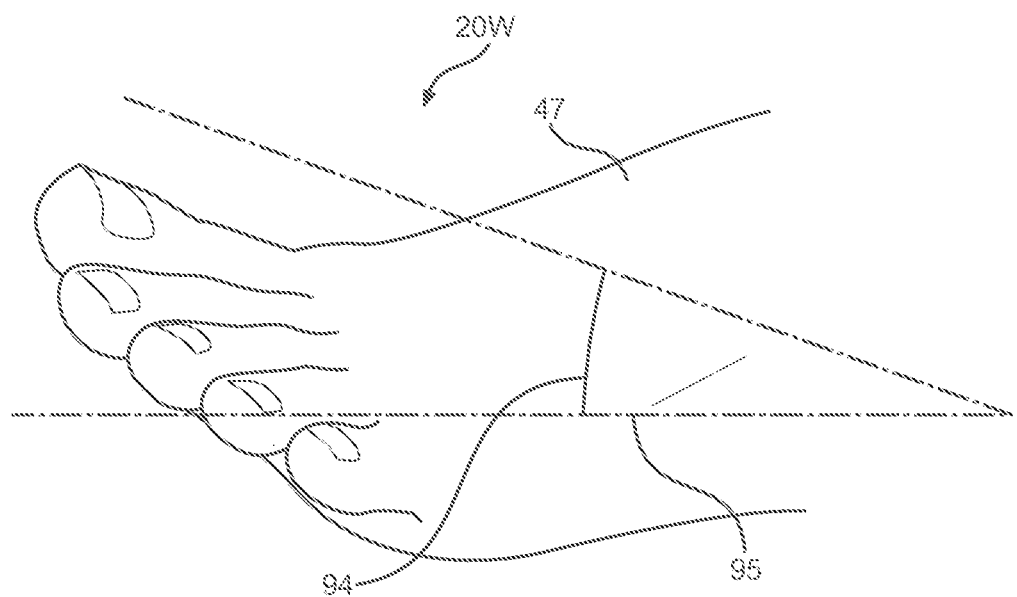

In another step in the fourth embodiment is to is to orient a user's body to a predetermined orientation 20W simultaneously with predetermined orientations 20O, 20P, 20Q, 20R, 20S, 20T, 20U, and 20V. FIGS. 15A-15B illustrate the predetermined orientation 20W of a user's 47 body having positioning of at least one toe 92 of user 47 between 0-45 degrees of flexion 93 (FIG. 15A) or between 0-45 degrees of extension 94 (FIG. 15B). It is within the scope of this invention for first predetermined location on the user's body to be at least a portion of a foot. It is within the scope of this invention for the garment to emit a vibration to the first predetermined location on a user's body. It is within the scope of this invention for the garment to be pneumatically actuated to intermittently constrict a first predetermined location on the user's body. The garment may be electrically conductive sock 96 (FIG. 14B).

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

The invention claimed is:

1. A method of stimulation of a body of a user, comprising the steps of:
    providing a stimulator, said stimulator is connected to a garment, said garment is connected to a first predetermined location on a user's body;
    positioning a user's body at a predetermined orientation, whereby, said predetermined orientation comprising the steps of:
    positioning at least one finger of said user between 0-120 degrees of flexion or between 0-35 degrees of extension;
    positioning at least one wrist of said user between 0-50 degrees of extension or 0-85 degrees of flexion;
    positioning said at least one wrist of said user between 0-88 degrees of pronation or between 0-88 degrees of supination;
    positioning said at least one wrist of said user between 0-28 degrees of ulnar deviation or between 0-18 degrees of radial deviation;
    positioning at least one elbow of said user between 0--3 degrees of hyperextension or between 0-130 degrees of flexion;
    positioning at least one shoulder of said user between 0-145 degrees of shoulder abduction or between 0-45 degrees of shoulder adduction;
    positioning said at least one shoulder of said user between 0-145 degrees of shoulder flexion or between 0-58 degrees of extension; and,
    positioning said at least one shoulder of said user between 0-85 degrees shoulder of external rotation or between 0-50 degrees of internal rotation; and,
    applying stimulation from said stimulator to said first predetermined location on said user's body, whereby, therapeutic effects are experienced at said first predetermined location and at a second predetermined location.

2. The method of stimulation of a body of a user of claim 1, wherein said first predetermined location on said user's body is at least a portion of an arm.

3. The method of stimulation of a body of a user of claim 1, wherein said first predetermined location on said user's body is at least a portion of a finger.

4. The method of stimulation of a body of a user of claim 1, wherein said first predetermined location on said user's body is at least one hand.

5. The method of stimulation of a body of a user of claim 1, wherein said first predetermined location on said user's body is at least a portion of a shoulder.

6. The method of stimulation of the body for pain relief of claim 1, wherein said garment is pneumatically actuated to constrict said first predetermined location on said user's body.

7. A method of stimulation of a body of a user, comprising the steps of:
    providing a stimulator, said stimulator is connected to a garment, said garment is connected to a first predetermined location on a user's body;
    positioning a user's body at a predetermined orientation, whereby, said predetermined orientation comprising the steps of:
    positioning a neck of said user between 0-80 degrees of left rotation or between 0-80 degrees of right rotation;
    positioning neck of said user between 0-65 degrees of flexion or between 0-55 degrees of extension; and,
    positioning said neck of said user between 0-45 degrees of right lateral flexion or between 0-45 degrees of left lateral flexion; and,
    applying stimulation from said stimulator to said first predetermined location on said user's body, whereby, therapeutic effects are experienced at said first predetermined location and at a second predetermined location.

8. The method of stimulation of a body of a user of claim 7, wherein said first predetermined location on said user's body is at least a portion of said neck.

9. The method of stimulation of a body of a user of claim 7, wherein said first predetermined location on said user's body is at least a portion of a head of said user.

10. The method of stimulation of a body of a user of claim 7, wherein said garment is pneumatically actuated to constrict said first predetermined location on said user's body.

11. The method of stimulation of a body of a user of claim 7, wherein positioning a thoracic spine of said user between 0-50 degrees of right rotation or between 0-50 degrees of left rotation, positioning said thoracic spine of said user between 0-90 degrees of flexion or 0-45 degrees of extension, and positioning said thoracic spine of said user between 0-40 degrees of right lateral flexion or between 0-40 degrees of left lateral flexion.

12. The method of stimulation of a body of a user of claim 11, wherein said first predetermined location on said user's body is at least a portion of a spine.

13. The method of stimulation of a body of a user of claim 11, wherein positioning a lumbar spine of said user between 0-55 degrees of right rotation or between 0-55 degrees of left rotation, positioning said lumbar spine of said user between 0-110 degrees of flexion or between 0-50 degrees of extension, positioning said lumbar spine of said user between 0-50 degrees of right lateral flexion or between 0-50 degrees of left lateral flexion.

14. The method of stimulation of a body of a user of claim 13, wherein said first predetermined location on said user's body is at least a portion of a spine.

15. The method of stimulation of a body of a user of claim 13, wherein said first predetermined location on said user's body is at least a portion of an abdomen.

16. A method of stimulation of a body of a user, comprising the steps of:
  providing a stimulator, said stimulator is connected to a garment, said garment is connected to a first predetermined location on a user's body;
  positioning a user's body at a predetermined orientation, whereby, said predetermined orientation comprising the steps of:
  positioning a lumbar spine of said user between 0-55 degrees of right rotation or between 0-55 degrees of left rotation;
  positioning said lumbar spine of said user between 0-110 degrees of flexion or between 0-50 degrees of extension;
  positioning said lumbar spine of said user between 0-50 degrees of right lateral flexion or between 0-50 degrees of left lateral flexion;
  positioning a thoracic spine of said user between 0-50 degrees of right rotation or between 0-50 degrees of left rotation;
  positioning said thoracic spine of said user between 0-90 degrees of flexion or 0-45 degrees of extension;
  positioning said thoracic spine of said user between 0-40 degrees of right lateral flexion or between 0-40 degrees of left lateral flexion;
  positioning a hip of said user between 0-38 degrees of internal rotation or between 0-38 degrees of external rotation; and,
  positioning said hip of said user between 0-40 degrees of extension or between 0-130 degrees of flexion; and,
  applying stimulation from said stimulator to said first predetermined location on said user's body, whereby, therapeutic effects are experienced at said first predetermined location and at a second predetermined location.

17. The method of stimulation of a body of a user of claim 16, wherein said first predetermined location on said user's body is at least a portion of a pelvis.

18. The method of stimulation of a body of a user of claim 16, wherein said first predetermined location on said user's body is at least a portion of a sacrum.

19. The method of stimulation of a body of a user of claim 16, wherein said first predetermined location on said user's body is at least a portion of glutes.

20. A method of stimulation of a body of a user, comprising the steps of:
  providing a stimulator, said stimulator is connected to a garment, said garment is connected to a first predetermined location on a user's body;
  positioning a user's body at a predetermined orientation, whereby, said predetermined orientation comprising the steps of:
  positioning a lumbar spine of said user between 0-55 degrees of right rotation or between 0-55 degrees of left rotation;
  positioning said lumbar spine of said user between 0-110 degrees of flexion or between 0-50 degrees of extension;
  positioning said lumbar spine of said user between 0-50 degrees of right lateral flexion or between 0-50 degrees of left lateral flexion;
  positioning a hip of said user between 0-38 degrees of internal rotation or between 0-38 degrees of external rotation;
  positioning said hip of said user between 0-40 degrees of extension or between 0-130 degrees of flexion;
  positioning said knee of said user between 0--5 degrees of hyperextension or between 0-125 degrees of flexion;
  positioning an ankle of said user between 0-14 degrees of dorsiflexion or between 0-55 degrees of plantar flexion; and,
  positioning said ankle of said user between 0-35 degrees of inversion or between 0-25 degrees of eversion; and,
  applying stimulation from said stimulator to said first predetermined location on said user's body, whereby, therapeutic effects are experienced at said first predetermined location and at a second predetermined location.

21. The method of stimulation of a body of a user of claim 20, wherein said first predetermined location on said user's body is at least a portion of a leg.

22. The method of stimulation of a body of a user of claim 20, wherein positioning at least one toe of said user between 0-45 degrees of flexion or between 0-45 degrees of extension.

23. The method of stimulation of a body of a user of claim 22, wherein said first predetermined location on said user's body is at least a portion of a foot.

24. The method of stimulation of a body of a user of claim 20, wherein said garment is pneumatically actuated to constrict said first predetermined location on said user's body.

* * * * *